United States Patent [19]

Nagashima

[11] Patent Number: 5,335,664
[45] Date of Patent: Aug. 9, 1994

[54] MONITOR SYSTEM AND BIOLOGICAL SIGNAL TRANSMITTER THEREFOR

[75] Inventor: Sadao Nagashima, Tokorozawa, Japan

[73] Assignee: Casio Computer Co., Ltd., Tokyo, Japan

[21] Appl. No.: 940,181

[22] Filed: Sep. 3, 1992

[30] Foreign Application Priority Data

Sep. 17, 1991 [JP] Japan .................................. 3-235882
Sep. 17, 1991 [JP] Japan .................................. 3-235883
Dec. 24, 1991 [JP] Japan .................................. 3-341310

[51] Int. Cl.$^5$ ............................................. A61B 5/04
[52] U.S. Cl. ....................................... 128/696; 128/903
[58] Field of Search ............... 728/696, 702, 705, 706, 728/903, 904

[56] References Cited

U.S. PATENT DOCUMENTS

| | | | |
|---|---|---|---|
| 3,426,150 | 2/1969 | Tygart | 128/696 |
| 3,572,316 | 3/1971 | Vogelman et al. | 128/903 |
| 3,603,881 | 9/1971 | Thornton | 128/903 |
| 3,724,455 | 4/1973 | Unger | 128/705 |
| 3,726,270 | 4/1973 | Griffis et al. | 128/904 |
| 3,882,277 | 5/1975 | DePedro et al. | 128/903 |
| 3,898,984 | 8/1975 | Mandel et al. | 128/696 |
| 3,902,478 | 9/1975 | Konopasek et al. | |
| 3,920,005 | 11/1975 | Gombrich et al. | 128/904 |
| 3,972,320 | 8/1976 | Kalman | 128/706 |
| 4,102,332 | 7/1978 | Gessman | 128/702 |
| 4,173,971 | 11/1979 | Karz | 128/904 |
| 4,698,848 | 10/1987 | Buckley | 128/696 |
| 4,854,328 | 8/1989 | Pollack . | |
| 4,958,645 | 9/1990 | Cadell et al. | |
| 5,036,869 | 8/1991 | Inahara . | |
| 5,058,597 | 10/1991 | Onoda et al. | 128/696 |

FOREIGN PATENT DOCUMENTS

0472411A1 2/1992 European Pat. Off. .
WO90/09143 9/1990 World Int. Prop. O. .

*Primary Examiner*—William E. Kamm
*Attorney, Agent, or Firm*—Frishauf, Holtz, Goodman & Woodward

[57] ABSTRACT

Biological signals detected by biological signal detecting units put on a plurality of persons to be monitored are transmitted to a plurality of wristwatches. The transmitted biological signals and ID code data corresponding to the biological signals are transmitted in the form of radio signals. A receiver unit receives the biological signals and the ID code data transmitted from the wristwatches and sends them to a monitor unit. The monitor unit displays the transmitted biological signals in a one-to-one correspondence with the ID code data, Upon detecting an abnormality in a given biological signal, the monitor unit generates an alarm sound. If a corresponding person to be monitored determines that the alarm sound is erroneously generated, he or she stops the alarm sound by manipulating a switch. If the person determines that the alarm sound is not a false alarm, his or her wristwatch transmits a contact designation signal and ID code data by a radio signal. On the basis of the contact designation signal and the ID code data, the receiver unit automatically activates an auto-dialing unit to inform the third person of the state of emergency.

8 Claims, 16 Drawing Sheets

FIG.8
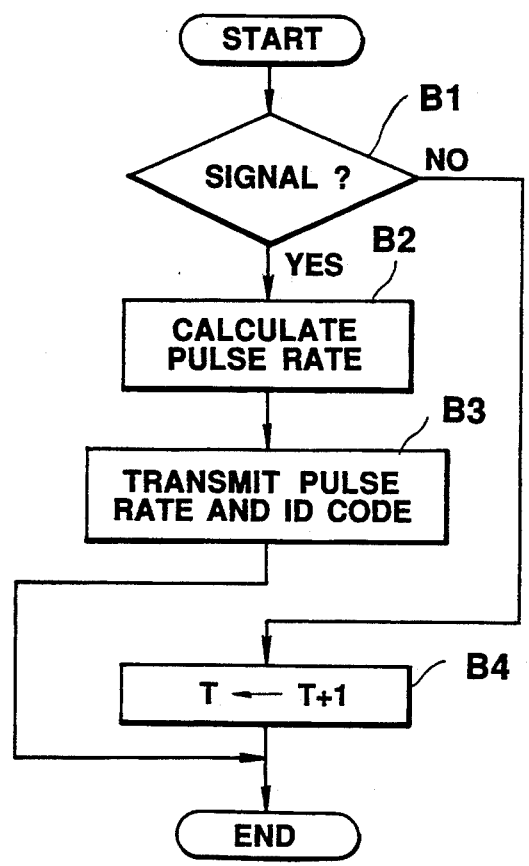
FIG.9A
FIG.9B
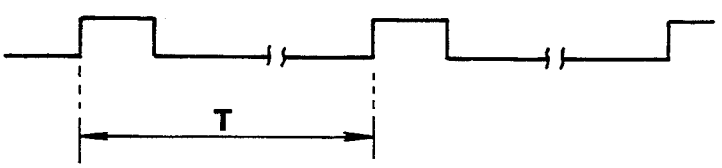
FIG.9C

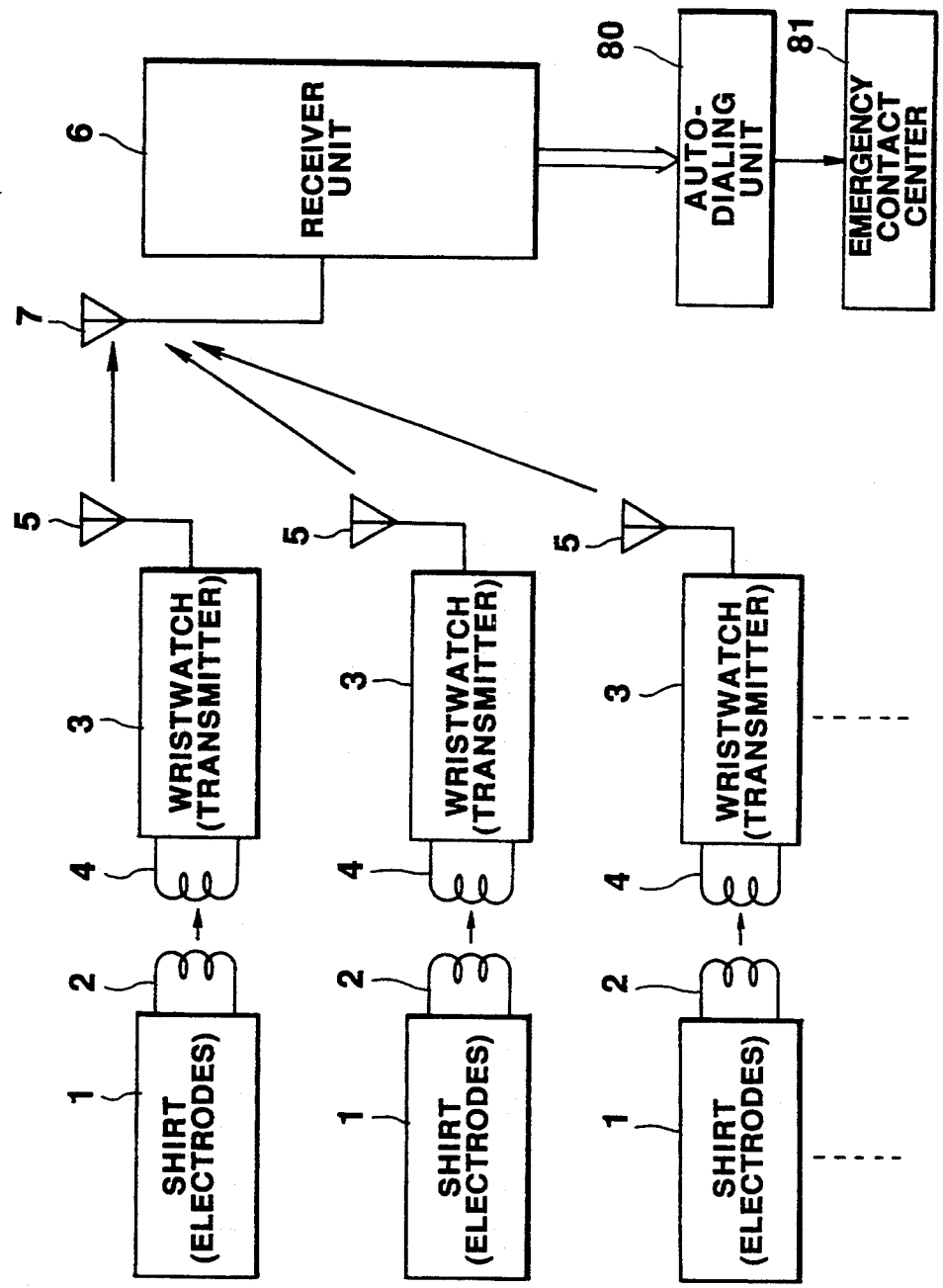

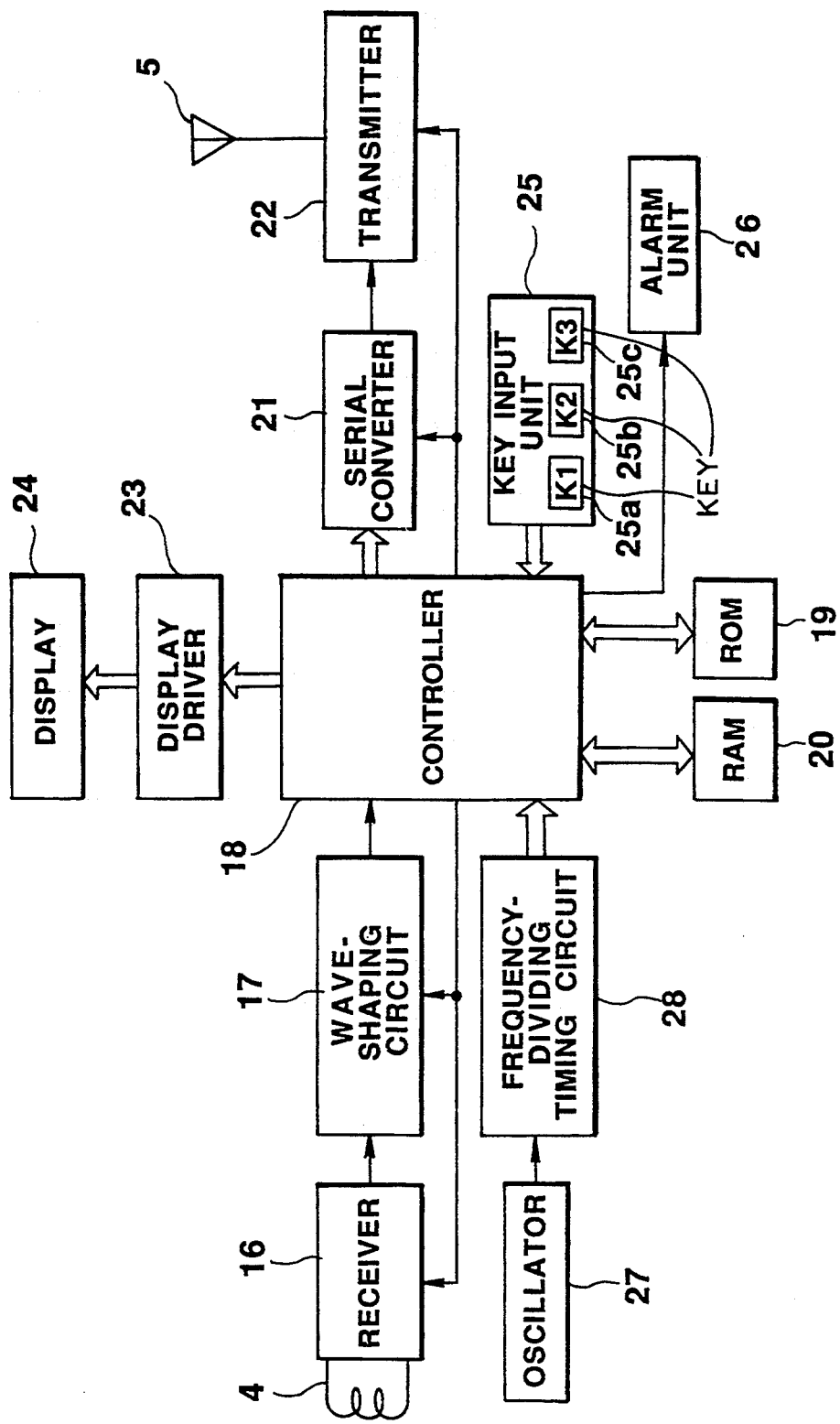

MONITOR SYSTEM AND BIOLOGICAL SIGNAL TRANSMITTER THEREFOR

BACKGROUND OF THE INVENTION

1. Field of the Invention

The present invention relates to a monitor system capable of monitoring signals or information (to be referred to as biological signals or biological information hereinafter) indicating conditions of a living body, such as an electrocardiogram waveform, a heart rate, and a blood pressure, of a person (object) to be monitored, e.g., a patient, and a biological signal transmitter used in this system.

2. Description of the Related Art

For patients who take exercises for rehabilitation or who get therapeutic exercises, it is necessary to monitor a biological signal or biological information, such as a heart rate, a pulse rate, or a blood pressure, during the exercises in order to exercise effectively and safely. This is also required for athletes who take hard exercises or people who get exercises for the purpose of promotion of health or physical fitness.

An ergometer is conventionally known as a device for this purpose. That is, a pulse rate sensor is put on an earlobe of a person to be monitored, and a change in a bloodstream or the like sensed by the pulse rate sensor is optically detected, thereby monitoring the pulse rate of the person during a so-called "aerobike" exercise. The ergometer thus evaluates the load of exercise on the person to be monitored or evaluates his or her physical strength.

This conventional ergometer, however, is generally so manufactured that a person to be monitored himself or herself monitors his or her own load of exercise or physical strength. Therefore, it is impossible for the third person, such as a doctor or a trainer, to simultaneously or individually monitor heart rates, blood pressures, or the like of a large number of persons to be monitored.

SUMMARY OF THE INVENTION

The present invention has been made to solve the above conventional problems.

It is, therefore, an object of the present invention to provide a monitor system capable of monitoring a biological signal or biological information, such as an electrocardiogram waveform, a heart rate, or a blood pressure, of a person to be monitored, and a biological signal transmitter used in this system.

It is another object of the present invention to provide a monitor system capable of simultaneously or individually monitoring pieces of biological information, such as pulse rates, of a plurality of persons to be monitored.

It is still another object of the present invention to provide a monitor system capable of simultaneously monitoring pieces of biological information, such as pulse rates, of a plurality of persons to be monitored, and upon detecting occurrence of an abnormality in a given person to be monitored, automatically making contact with an emergency contact center or the like by phone, thereby informing the center of the state of emergency of the person having the abnormality.

It is still another object of the present invention to provide a monitor system capable of detecting biological information, such as a pulse rate, of a person to be monitored, and reliably informing the third person of the detected biological information without errors.

In order to achieve the above objects, the present invention adopts the following arrangements.

That is, one arrangement of the present invention comprises a plurality of biological signal detecting means, to be put on a plurality of human bodies, for individually detecting biological signals generated by the human bodies, a plurality of first transmitting means each for transmitting the biological signal detected by a corresponding one of the biological signal detecting means, a plurality of second transmitting means each for receiving the biological signal transmitted from a corresponding one of the first transmitting means and transmitting an ID code signal predetermined in correspondence with the received biological signal together with the biological signal in the form of a radio signal, and monitor means for receiving the radio signal transmitted from the plurality of second transmitting means and monitoring pieces of biological information corresponding to the biological signals transmitted in the form of radio signals in a one-to-one correspondence with the ID code signals.

Another arrangement of the present invention is a biological signal transmitter, to be put on a human body, for receiving an input biological signal from output means for detecting a biological signal generated by the human body and outputting the detected biological signal, and transmitting the received biological signal in the form of a radio signal to monitor means for monitoring the content of the biological signal, the biological signal transmitter comprising receiving means for receiving the input biological signal from the output means, and transmitting means for transmitting the biological signal received by the receiving means together with an ID code signal predetermined in correspondence with the received biological signal in the form of a radio signal to the monitor means.

Still another arrangement of the present invention comprises a plurality of biological signal detecting means, to be put on a plurality of human bodies, for individually detecting biological signals generated by the human bodies, a plurality of first transmitting means each for transmitting the biological signal detected by a corresponding one of the biological signal detecting means, a plurality of second transmitting means each for receiving the biological signal transmitted from a corresponding one of the first transmitting means, determining whether a value of the received biological signal is an abnormal value, and if an abnormality is detected, transmitting the biological signal having the abnormality together with an ID code signal predetermined in correspondence with the received biological signal in the form of a radio signal, and monitor means for receiving the radio signal transmitted from the plurality of second transmitting means and monitoring pieces of biological information corresponding to the biological signals transmitted in the form of radio signals in a one-to-one correspondence with the ID code signals.

Still another arrangement of the present invention is a biological signal transmitter, to be put on a human body, for receiving an input biological signal from output means for detecting a biological signal generated by the human body and outputting the detected biological signal, and transmitting the received biological signal in the form of a radio signal to monitor means for monitoring the content of the biological signal, the biological signal transmitter comprising receiving means for receiving the input biological signal from the output means, abnormality determining means for determining whether a value of the biological signal received by the receiving means is an abnormal value, and transmitting means for transmitting, if an abnormality is determined by the abnormality determining means, the biological signal having the abnormality together with an ID code signal predetermined in correspondence with the received biological signal in the form of a radio signal to the monitor means.

Still another arrangement of the present invention comprises biological signal detecting means to be put on a human body to sequentially detect biological signals generated by the human body, first transmitting means for patterning the biological signals, sequentially detected by the biological signal detecting means, in accordance with a predetermined rule and sequentially transmitting the patterned biological signals in the form of radio signals, determining means for determining whether the biological signals sequentially transmitted in the form of radio signals from the transmitting means are biological signals patterned in accordance with the rule, calculating means for calculating a value of biological information corresponding to the patterned biological signals if the determining means determines that the biological signals sequentially transmitted from the transmitting means are the biological signals patterned in accordance with the rule, and display means for displaying the value of the biological information calculated by the calculating means.

Still another arrangement of the present invention comprises biological signal detecting means to be put on a human body to sequentially detect biological signals generated by the human body, first transmitting means for patterning the biological signals, sequentially detected by the biological signal detecting means, in accordance with a predetermined rule and sequentially transmitting the patterned biological signals in the form of radio signals, determining means for determining whether the biological signals sequentially transmitted in the form of radio signals from the transmitting means are biological signals patterned in accordance with the rule, calculating means for calculating a value of biological information corresponding to the patterned biological signals if the determining means determines that the biological signals sequentially transmitted from the transmitting means are the biological signals patterned in accordance with the rule, discriminating means for discriminating whether the value of the biological information calculated by the calculating means falls within a predetermined range, and alarming means for, if the discriminating means discriminates that the value of the biological information calculated by the calculating means falls within the predetermined range, displaying the biological information calculated by the calculating means and if the discriminating means discriminates that the value of the biological information calculated by the calculating means falls outside the predetermined range, generating an alarm sound indicating that the value of the biological information calculated by the calculating means is an abnormal value.

Still another arrangement of the present invention comprises biological signal detecting means to be put on a human body to sequentially detect biological signals generated by the human body, radio signal transmitting means for sequentially transmitting the biological signals sequentially detected by the biological signal detecting means in the form of radio signals, radio signal receiving means for receiving the biological signals sequentially transmitted in the form of radio signals from the radio signal transmitting means, determining means for determining whether the biological signals sequentially received by the radio signal receiving means correspond to the biological signals sequentially detected by the biological signal detecting means, calculating means for calculating a value of biological information corresponding to the received biological signals if the determining means determines that the biological signals sequentially received by the radio signal receiving means correspond to the biological signals sequentially detected by the biological signal detecting means, and display means for displaying the value of the biological information calculated by the calculating means.

Still another arrangement of the present invention comprises biological signal detecting means to be put on a human body to sequentially detect biological signals generated by the human body, radio signal transmitting means for sequentially transmitting the biological signals sequentially detected by the biological signal detecting means in the form of radio signals, radio signal receiving means for receiving the biological signals sequentially transmitted in the form of radio signals from the radio signal transmitting means, determining means for determining whether the biological signals sequentially received by the radio signal receiving means correspond to the biological signals sequentially detected by the biological signal detecting means, calculating means for calculating a value of biological information corresponding to the received biological signals if the determining means determines that the biological signals sequentially received by the radio signal receiving means correspond to the biological signals sequentially detected by the biological signal detecting means, discriminating means for discriminating whether the value of the biological information calculated by the calculating means falls within a predetermined range, and alarming means for, if the discriminating means discriminates that the value of the biological information calculated by the calculating means falls within the predetermined range, displaying the biological information calculated by the calculating means and if the discriminating means discriminates that the value of the biological information calculated by the calculating means falls outside the predetermined range, generating an alarm sound indicating that the value of the biological information calculated by the calculating means is an abnormal value.

Still another arrangement of the present invention is a biological signal transmitter for sequentially receiving biological signals in the form of radio signals sequentially detected by biological signal detecting means put on a human body to sequentially detect the biological signals generated by the human body, and sequentially transmitting, in the form of radio signals, the biological signals sequentially received in the form of radio signals, the biological signal transmitter comprising radio signal receiving means for sequentially receiving the biological signals sequentially detected by the biological signal detecting means in the form of radio signals, and biological signal transmitting means for converting the biological signals sequentially received in the form of radio signals by the radio signal receiving means into biological signals patterned in accordance with a predetermined rule, and sequentially transmitting the converted biological signals in the form of radio signals.

BRIEF DESCRIPTION OF THE DRAWINGS

FIG. 8 is a flow chart for explaining the operation of the controller;

FIGS. 9A to 9C are timing charts showing waveforms of an electrocardiogram waveform signal and the like;

FIG. 10 is a block diagram showing a monitor system according to another embodiment of the present invention;

FIG. 11 is a block diagram showing the circuit configuration of a wristwatch shown in FIG. 10;

DETAILED DESCRIPTION OF THE PREFERRED EMBODIMENTS

An embodiment of the present invention will be described below with reference to FIGS. 1 to 9C.

Figure 1:
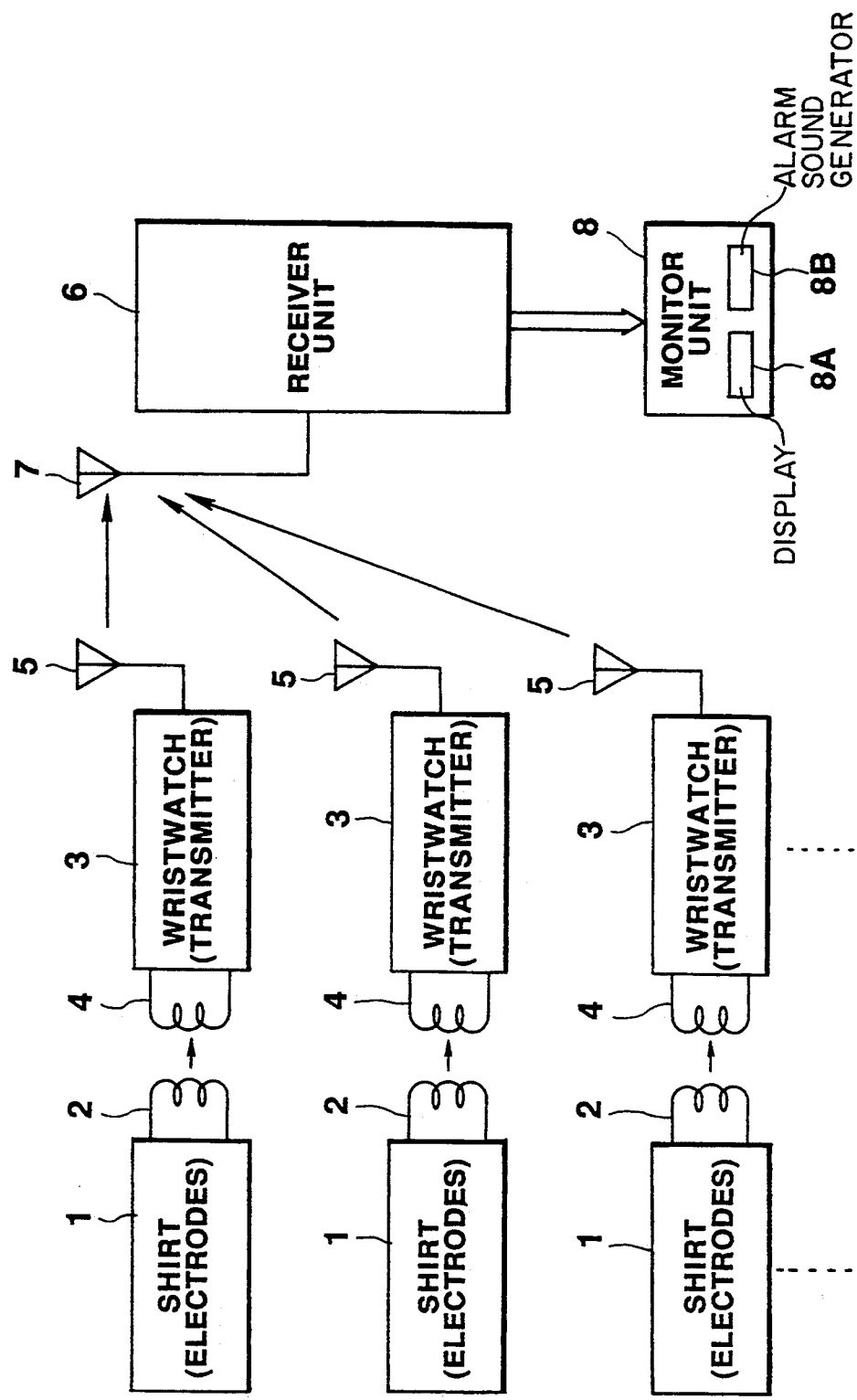
FIG. 1 is a block diagram showing a monitor system to which the present invention is applied.

FIG. 1 is a block diagram showing the arrangement of a monitor system to which the present invention is applied.

This monitor system simultaneously monitors pulse rates of a plurality of persons to be monitored (e.g., patients in a hospital).

Figure 2:
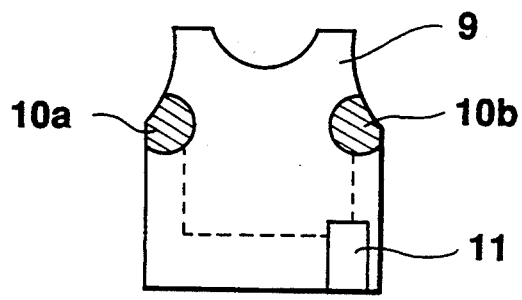
FIG. 2 is a view showing the arrangement of a shirt used in the monitor system.
Figure 3:
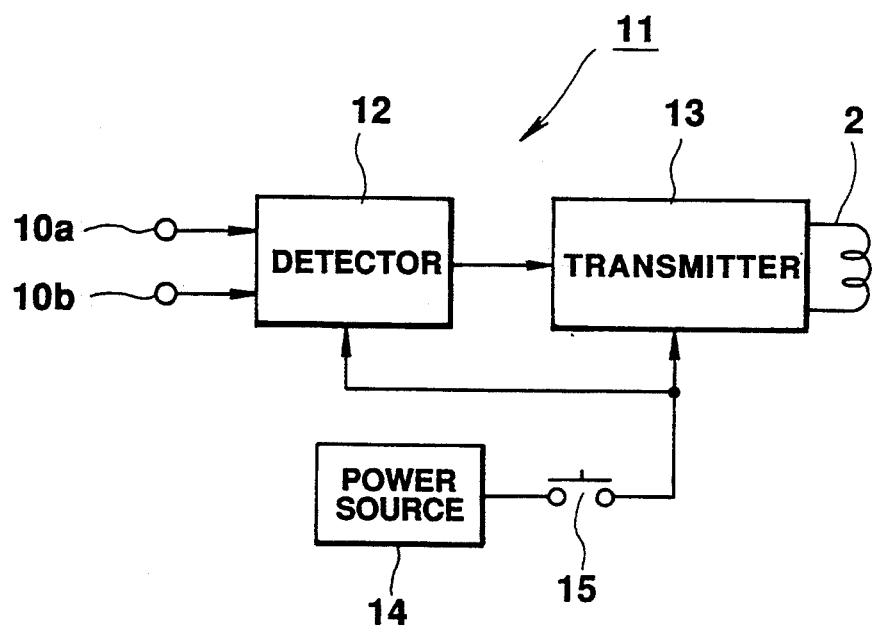
FIG. 3 is a block diagram showing the circuit configuration of an electronic circuit incorporated in the shirt.

A plurality of shirts 1 as shown in FIG. 2 are put on a plurality of persons to be monitored. As shown in FIG. 3, each shirt 1 comprises a detector 12 including a pair of electrodes 10a and 10b for detecting a biological signal, such as an electrocardiogram waveform, generated by a person to be monitored, and a transmitter 13 including a coil 2 for transmitting the biological signal detected by the detector 12 in the form of an electromagnetic induction signal.

A plurality of wristwatches 3 are put on wrists of a plurality of persons to be monitored who wear the shirts 1. Each wristwatch 3 comprises a coil 4 for receiving the electromagnetic induction biological signal transmitted from the coil 2 of the shirt 1 and an antenna 5 for transmitting a pulse rate signal obtained on the basis of the received biological signal in the form of a radio signal.

Figure 4:
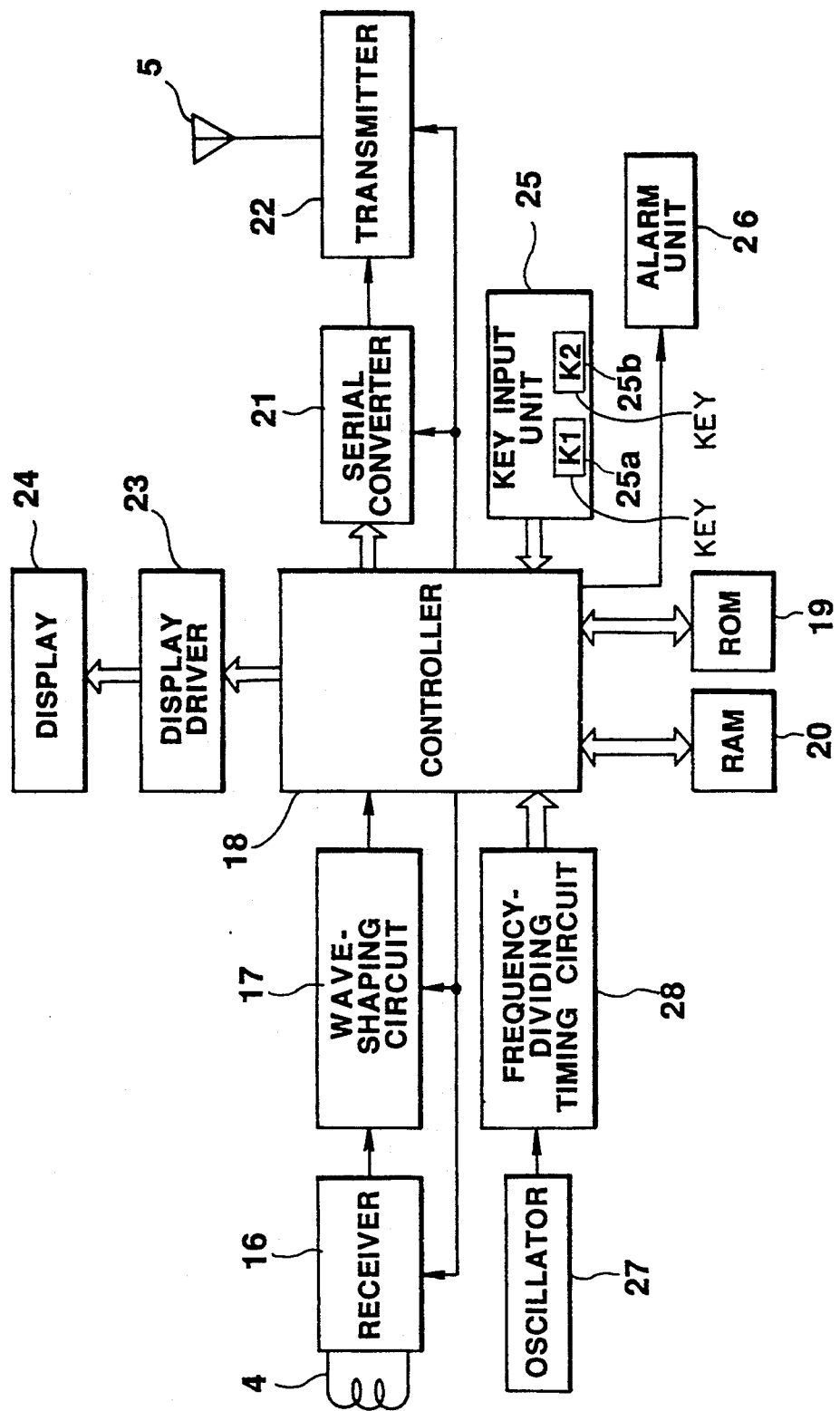
FIG. 4 is a block diagram showing the circuit configuration of a wristwatch used in the monitor system.

In each of the wristwatches 3, specific identification (ID) code information for distinguishing a corresponding person to be monitored from another is set in an internal RAM 20 shown in FIG. 4. On the basis of a biological signal transmitted from the shirt 1, the wristwatch 3 generates pulse rate data of a corresponding person to be monitored, converts the generated pulse rate data and the corresponding ID code data into a radio signal, and transmits the radio signal from the antenna 5.

A receiver unit 6 receives the pulse rate data and the ID code data of a person to be monitored transmitted from each of the wristwatches 3 through an antenna 7 and sends them to a monitor unit 8.

The monitor unit 8 simultaneously displays a plurality of pairs of the pulse rate data and the ID code data sent from the receiver unit 6 on a display 8A such as a CRT or a liquid crystal display, thereby monitoring the respective pulse rates of the persons (e.g., patients in a hospital) at the same time.

FIG. 2 is a view showing the arrangement of the shirt 1 used in the monitor system shown in FIG. 1.

A shirt main body 9 has a shape of, e.g., an athletic-style shirt. The pair of electrodes 10a and 10b are arranged at the right and left underarm positions of the shirt main body 9 and brought into contact with the skin of a person to be monitored having the shirt 1 on. The electrodes 10a and 10b detect an electrocardiogram waveform as a biological signal generated by the heart of the person and sends the detected biological signal to an electronic circuit 11 provided at an underarm position or a waist position of the shirt main body 9. The electronic circuit 11 transmits the detected biological signal in the form of a radio signal using electromagnetic induction from the coil 2 to the wristwatch 3. The signal may also be transmitted to the wristwatch 3 by a wire system using a connecting cord or the like.

FIG. 3 is a block diagram showing the circuit configuration of the electronic circuit 11 of the shirt 1.

The pair of electrodes 10a and 10b for detecting an electrocardiogram waveform generated by the heart of a person to be monitored are connected to the detector 12 and send an electrocardiogram waveform signal to the detector 12. The detector 12 amplifies the input electrocardiogram waveform signal from the electrodes 10a and 10b and sends the amplified electrocardiogram waveform signal to the transmitter 13.

This electrocardiogram waveform signal is, for example, a signal having a waveform as shown in FIG. 9A. The transmitter 13 converts the input electrocardiogram waveform signal from the detector 12 into an electromagnetic induction signal and transmits the converted signal from the coil 2. The electrocardiogram waveform signal in the form of the electromagnetic induction signal transmitted from the transmitter 13 is, for example, a signal having a waveform as shown in FIG. 9B. This electrocardiogram waveform signal can be received satisfactorily within a distance of up to about two meters. A power source 14 contains a battery or the like and supplies a drive voltage to the detector 12 and the transmitter 13 via a power switch 15.

FIG. 4 is a block diagram showing the circuit configuration of the wristwatch 3 used in the monitor system shown in FIG. 1.

The coil 4 is a detecting coil for detecting the electrocardiogram waveform signal in the form of the electromagnetic induction signal transmitted from the coil 2 and is connected to a receiver 16. The receiver 16 receives the electrocardiogram waveform signal detected by the coil 4 and outputs the received biological signal to a wave-shaping circuit 17. The wave-shaping circuit 17 wave-shapes the input biological signal from the receiver 16 to convert it into a rectangular wave signal as shown in FIG. 9C and outputs the converted signal to a controller 18. Note that the receiver 16 and the wave-shaping circuit 17 start their operations in accordance with operation signals supplied from the controller 18.

The controller 18 is a central processing unit (CPU) for controlling the individual sections on the basis of microprograms prestored in a ROM 19, thereby performing various types of processing. A RAM 20 is a memory for storing various data. The RAM 20 will be described in more detail later with reference to FIG. 6. A serial converter 21 converts pulse rate data and ID code data delivered in parallel from the controller 18 into a serial signal and sends the serial signal to a transmitter 22. The transmitter 22 converts the supplied serial signal into a radio signal and transmits the radio signal from the antenna 5. A display driver 23 outputs a display drive signal based on the input pulse rate data and ID code data from the controller 18 to a display 24, thereby driving the display 24. The display 24 comprises, e.g., liquid crystal display elements, and displays pulse rate data in a one-to-one correspondence with a plurality of ID code data. The display 24 also displays a current time or the like on the basis of an oscillator 27.

A key input unit 25 includes a K1 key 25a for pulse rate measurement, a K2 key 25b for setting ID code data, and other keys, and outputs a key input signal corresponding to a key manipulation to the controller 18. The K1 key 25a for pulse rate measurement is a key for inverting a flag register F0 (to be described later), thereby starting pulse rate measurement. The K2 key 25b for setting ID code data is a key for inverting a flag register F1 (to be described later), thereby setting ID code data.

An alarm unit 26 generates an alarm sound on the basis of an input alarm signal from the controller 18.

The oscillator 27 oscillates a clock signal of a predetermined frequency and applies the clock signal to a frequency-dividing/timing circuit 28. The frequency-dividing/timing circuit 28 frequency-divides the input clock signal from the oscillator 27 to generate various timing signals, such as a time-count signal, and supplies them to the controller 18.

Figure 5:
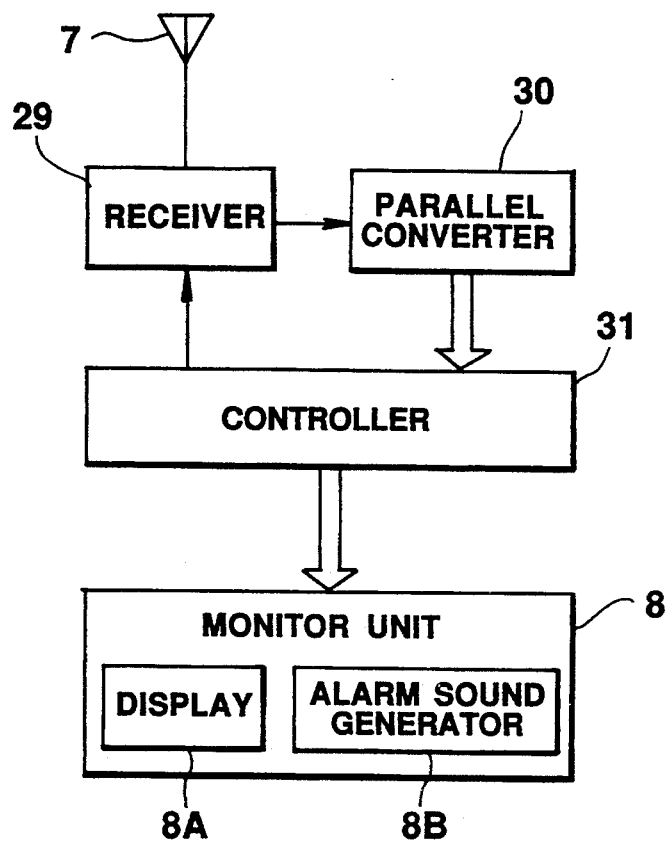
FIG. 5 is a block diagram showing the circuit configuration of a receiver unit and a monitor unit used in the monitor system.

FIG. 5 is a block diagram showing the circuit configuration of the receiver unit 6 and the monitor unit 8 used in the monitor system shown in FIG. 1.

The antenna 7 for receiving pulse rate data and ID code data in the form of a radio signal transmitted from the antenna 5 of each wristwatch 3 is connected to a receiver 29. The receiver 29 receives the radio signal detected by the antenna 7 and applies the received radio signal to a parallel converter 30. The parallel converter 30 converts the input radio signal from the receiver 29 into the pulse rate data and the ID code data in the form of parallel signals and applies the data to a controller 31. The receiver 29 performs its operation in accordance with an operation signal supplied from the controller 31. The controller 31 is a central processing unit (CPU) for controlling the individual sections on the basis of microprograms prestored in an internal ROM (not shown), thereby performing various types of processing. The controller 31 outputs the input pulse rate data and ID code data from the parallel converter 30 to the monitor unit 8. The monitor unit 8 includes the display 8A, such as a CRT or a liquid crystal display, for simultaneously displaying a plurality of pairs of the input pulse rate data and ID code data from the controller 31. The monitor unit 8 also includes an alarm sound generator 8B for generating an alarm sound when the value of input pulse rate data from the controller 31 reaches a predetermined value or falls outside a predetermined range.

Figure 6:
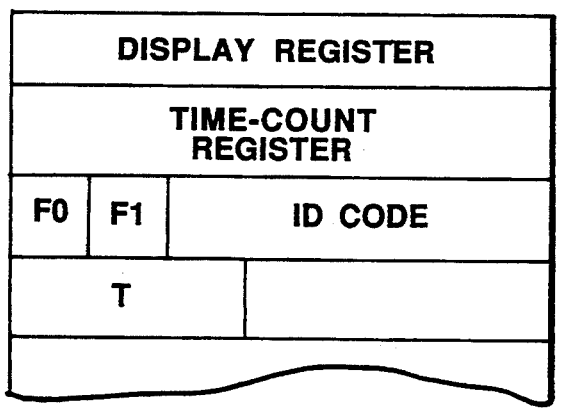
FIG. 6 is a view showing the memory format of a RAM used in the monitor system.

FIG. 6 is a view showing the memory format of the RAM 20 shown in FIG. 4.

Referring to FIG. 6, a display register stores data to be displayed on the display 24, and a time-count register stores current time data to be sequentially updated by time-count processing. The flag register F0 stores a flag indicating a condition of detection of a pulse rate signal, and the flag register F1 stores a flag indicating a condition of setting of ID code data.

An ID code register stores ID code data. The ID code data is, e.g., code data of eight bits set for each person to be monitored. Assume, for example, that ID code data for a person A to be monitored is "00000001" and ID code data for a person B to be monitored is "00000010".

A register T is for measuring a period T of a rectangular wave signal indicating an electrocardiogram waveform as shown in FIG. 9C. Note that the ID code data need not be stored in a RAM but may be stored in a ROM or a rewritable EEPROM.

The operations of this embodiment will be described below with reference to FIGS. 7 and 8.

Figure 7:
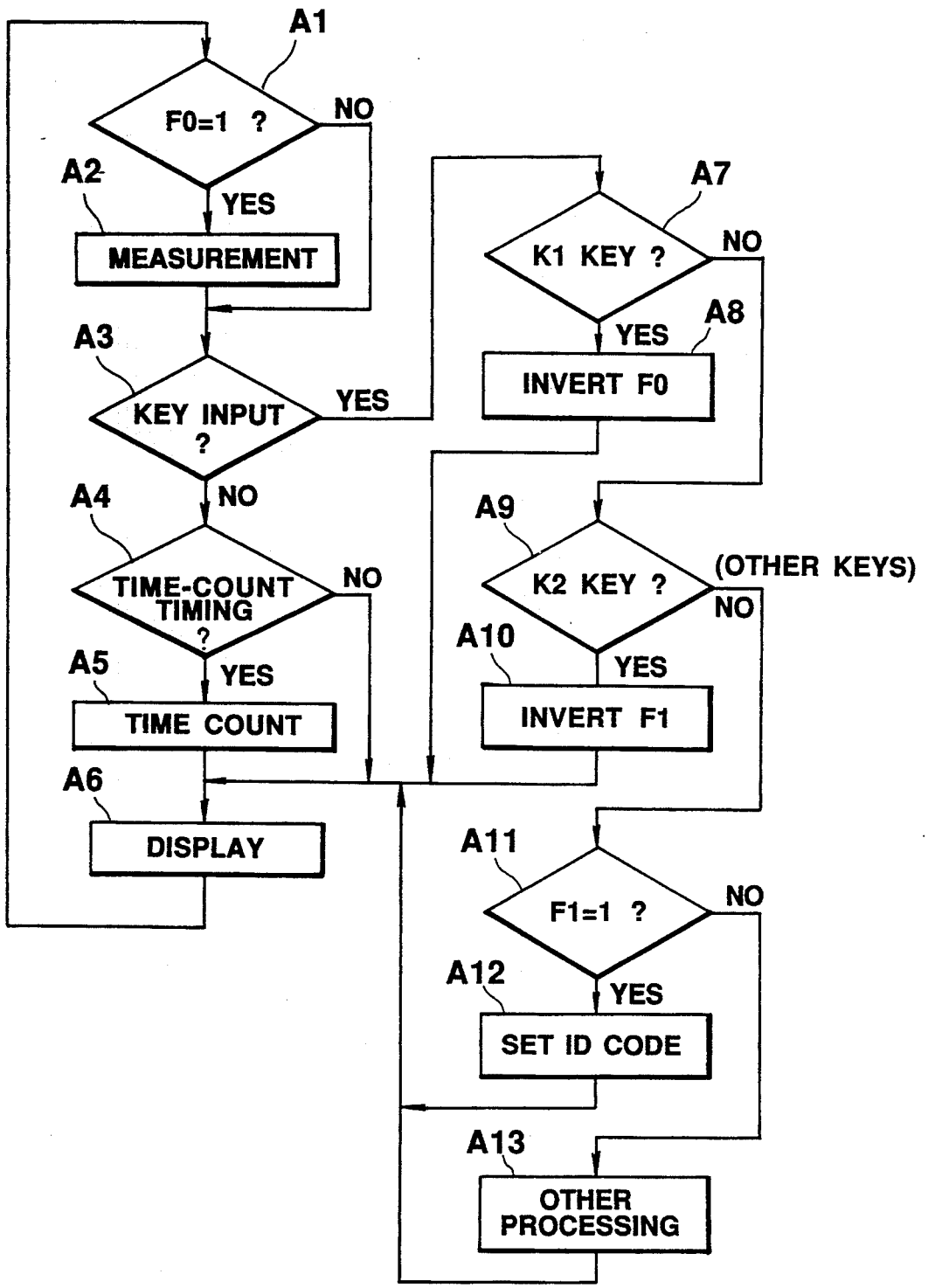
FIG. 7 is a flow chart for explaining the operation of a controller used in the monitor system.

FIG. 7 is a flow chart showing the overall operation of the wristwatch 3.

Referring to FIG. 7, the controller 18 checks in step A1 whether "F0=1", i.e., the content of the flag register F0 is "1". If YES is determined in step A1, the flow advances to step A2. If NO is determined in step A1, the flow advances to step A3. In this case, "F0=1" is determined if pulse rate measurement is set by the K1 key 25a for setting pulse rate measurement. Otherwise, "F0=0" is determined.

If "F0=1" is determined in step A1, the flow advances to step A2. In step A2, pulse rate measurement processing is executed. This pulse rate measurement processing will be described in detail later with reference to FIG. 8.

In step A3, the controller 18 checks whether a key input is present, i.e., the K1 key 25a for pulse rate measurement or the K2 key 25b for setting ID code data is manipulated. If YES in step A3, the flow advances to step A7. If NO in step A3, the flow advances to step A4.

If neither the K1 key 25a nor the K2 key 25b are manipulated, NO is determined in step A3, and the flow advances to step A4. In step A4, the controller 18 checks whether a time-count timing is set, i.e., a time-count signal is generated. If YES is determined in step A4, the flow advances to step A5. If NO is determined in step A4, the flow advances to step A6.

If the time-count timing is set in step A4, the flow advances to step A5 to execute time-count processing. That is, the current time data stored in the time-count register of the RAM 20 is updated.

In display processing in subsequent step A6, data stored in the display register is displayed on the display 24, and the flow returns to step A1.

If the K1 key 25a for pulse rate measurement, the K2 key 25b for setting ID code data, or another key is manipulated on the key input unit 25, the flow advances from step A3 to step A7. In step A7, the controller 18 checks whether the K1 key 25a is manipulated. If YES is determined in step A7, the flow advances to step A8. If NO is determined in step A7, the flow advances to step A9.

If manipulation of the K1 key 25a for pulse rate measurement is determined in step A7, the flow advances to step A8 to invert the content of the flag register F0 like "0→1" or "1→0". After executing the processing in step A8, the flow advances to the display processing in step A6.

If a key other than the K1 key 25a is manipulated, the flow advances from step A7 to step A9. In step A9, the controller 18 checks whether the K2 key 25b for setting ID code data is manipulated. If YES in step A9, the flow advances to step A10. If NO in step A9, the flow advances to step A11.

If manipulation of the K2 key 25b is determined in step A9, the flow advances to step A10 to invert the content of the flag register F1 like "0→1" or "1→0". After executing the processing in step A10, the flow advances to step A6.

If numeric keys are manipulated as other keys to input numerical data in step A9, the flow advances to step A11. In step A11, the controller 18 checks whether "F1=1", i.e., the content of the flag register F1 is "1". If YES in step A11, the flow advances to step A12. If NO in step A11, the flow advances to step A13.

If "F1=1" in step A11, this indicates that setting of ID code data is required, so the flow advances to step A12. In step A12, the input numerical data is stored as ID code data in the ID code register of the RAM 20. Thereafter, the flow advances from step A12 to step A6.

If "F1=1" is not determined in step A11, the flow advances to step A13 to execute other processing (e.g., time setting). Thereafter, the flow advances to step A6.

The details of the pulse rate measurement processing executed in step A2 will be described below with reference to FIG. 8.

In step B1, the controller 18 checks whether a biological signal is present.

That is, the controller 18 checks whether an electrocardiogram waveform signal transmitted by electromagnetic induction from the shirt 1 is detected by the coil 4. If YES is determined in step B1, the flow advances to step B2. If NO is determined in step B1, the flow advances to step B4.

If no electrocardiogram waveform signal is detected yet in step B1, the flow advances to step B4. In step B4, the content of the register T is incremented by one. That is, a period T from a preceding biological signal to a current biological signal is measured by the register T. After executing the processing in step B4, the pulse rate measurement processing shown in FIG. 8 is ended.

If a biological signal is detected, YES is determined in step B1, and processing in step B2 is executed. In step B2, pulse rate calculation processing is executed. That is, since the period T from a preceding biological signal to a current biological signal is measured by the register T, pulse rate data is calculated on the basis of this measured time.

In subsequent step B3, the transmitter 22 transmits the calculated pulse rate data and the ID code data stored in the RAM 20. That is, the controller 18 outputs the pulse rate data and the ID code data to the serial converter 21. The serial converter 21 converts the input pulse rate data and ID code data from the controller 18 into a serial signal and applies it to the transmitter 22. The transmitter 22 converts the input serial signal into a radio signal and transmits it from the antenna 5. After the transmission, the content of the register T is cleared.

The receiver unit 6 receives the radio signal of the pulse rate data and the ID code data by the antenna 7 and sends the received signal to the monitor unit 8. In this case, the receiver unit 6 distinguishes one pulse rate data from another on the basis of their ID code data. Therefore, even if pulse rate data are transmitted from a plurality of the wristwatches 3, pulse rate data of a given person to be monitored can be discriminated from that of another. The monitor unit 8 displays the received pulse rate data in a one-to-one correspondence with the ID code data on the display 8A. In this case, if the value of the pulse rate data of a given person to be monitored exceeds a predetermined value or range, the monitor unit 8 generates an alarm sound, for example, from the alarm sound generator 8B, thereby informing a doctor, a nurse, or an intensive care center of this abnormal value of the pulse rate data of the person.

According to this embodiment, it is possible to simultaneously detect a plurality of pieces of biological information, such as electrocardiogram waveforms, heart rates, or blood pressures and to simultaneously transmit pulse rate data as biological information of a plurality of persons to be monitored in a one-to-one correspondence with ID code data to the monitor unit 8. Therefore, a plurality of persons to be monitored can be reliably and easily monitored through the monitor unit 8.

FIG. 10 is a block diagram showing the arrangement of another embodiment of a monitor system to which the present invention is applied.

This monitor system simultaneously monitors pulse rates of a plurality of persons to be monitored. If an abnormality occurs in a pulse rate of a given person to be monitored, the monitor system automatically makes contact with a nurse, an emergency contact center, or the like by phone.

As in the above first embodiment, a plurality of shirts 1 are put on a plurality of persons to be monitored. Each shirt 1 includes a pair of electrodes 10a and 10b for detecting an electrocardiogram waveform signal as a biological signal of a person to be monitored having the shirt 1 on, and a coil 2 for transmitting the detected biological signal in the form of an electromagnetic induction signal.

A plurality of wristwatches 3 are put on wrists of persons to be monitored each having the shirt 1 on as in the first embodiment. Each wristwatch 3 includes a receiving coil 4 for receiving the electromagnetic induction biological signal transmitted from the shirt 1 and an antenna 5 for transmitting a contact designation signal for informing an abnormality in the form of a radio signal.

In each of a plurality of wristwatches 3, specific ID code data for distinguishing a corresponding person to be monitored from another is set in an internal RAM 20. The wristwatch 3 calculates pulse rate data on the basis of a biological signal transmitted from the shirt 1. If the pulse rate data falls outside a predetermined range, the wristwatch 3 generates an alarm sound for informing a corresponding person to be monitored of the abnormality. If the person determines that the alarm sound is erroneously generated, he or she stops the alarm sound by manipulating a K3 key 25c for stopping an alarm sound. If the person to be monitored himself or herself feels that the physical condition becomes worse, this means that the alarm sound is not a false alarm. Therefore, the person need not manipulate the K3 key 25c but just leaves the alarm generated.

If the K3 key 25c is not manipulated and a predetermined time (e.g., 30 seconds) has elapsed since the alarm sound is started to be generated, the wristwatch 3 automatically transmits a contact designation signal for informing the third person of the abnormality in a pulse rate together with ID code data for identifying the person to be monitored from the antenna in the form of a radio signal.

A receiver unit 6 receives the contact designation signals and the ID code data transmitted from a plurality of wristwatches 3 through an antenna 7 and sends the received contact designation signals and ID code data to an auto-dialing unit 80. The auto-dialing unit 80 is connected to a telephone line communicating with an emergency contact center 81 such as a nurse center. When the contact designation signal and the ID code data are sent from the receiver unit 6, the auto-dialing unit 80 automatically calls the emergency contact center 81 in accordance with a predetermined telephone number corresponding to the ID code data.

Note that the arrangement of the shirt 1 and the circuit configuration of an electronic circuit 11 provided in the shirt 1 are the same as those in the first embodiment described above.

The circuit configuration of the wristwatch 3 shown in FIG. 11 is also basically similar to that used in the above embodiment except that a key input unit 25 includes the K3 key 25c for stopping an alarm sound in addition to a K1 key 25a for pulse rate measurement, a K2 key 25b for setting ID code data, and other keys. The K3 key 25c for stopping an alarm sound is manipulated in order to stop an alarm sound currently being generated.

Figure 12:
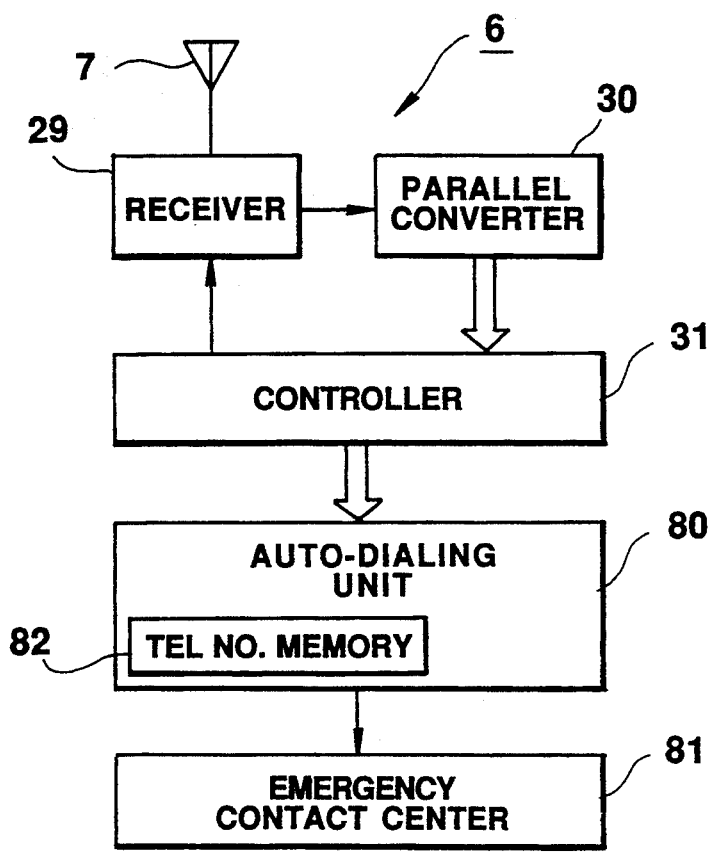
FIG. 12 is a block diagram showing the circuit configuration of a receiver unit and a monitor unit shown in FIG. 10.

FIG. 12 is a block diagram showing the circuit configuration of the receiver unit 6 and the auto-dialing unit 80. The antenna 7 is for receiving a contact designation signal and an ID code signal in the form of a radio signal transmitted from the antenna 5 of the wristwatch 3 and is connected to a receiver 29. The receiver 29 receives the radio signal detected by the antenna 7 and applies the received radio signal to a parallel converter 30. The parallel converter 30 converts the input radio signal from the receiver 29 into parallel signals and applies them to a controller 31. The receiver 29 performs its operation in accordance with an operation signal supplied from the controller 31. The controller 31 is a central processing unit (CPU) for controlling the individual sections on the basis of microprograms prestored in an internal ROM (not shown), thereby performing various types of processing. On the basis of the input parallel signals from the parallel converter 30, the controller 31 outputs the contact designation signal and the ID code data to the auto-dialing unit 80. The auto-dialing unit 80 prestores a plurality of telephone numbers in a one-to-one correspondence with the ID code data in a TEL NO. memory 82. When the controller 31 outputs the contact designation signal and the ID code data, the auto-dialing unit 80 reads out a telephone number corresponding to the ID code data from the TEL NO. memory 82 and automatically calls the emergency contact center 81 in accordance with the readout telephone number.

Figure 13:
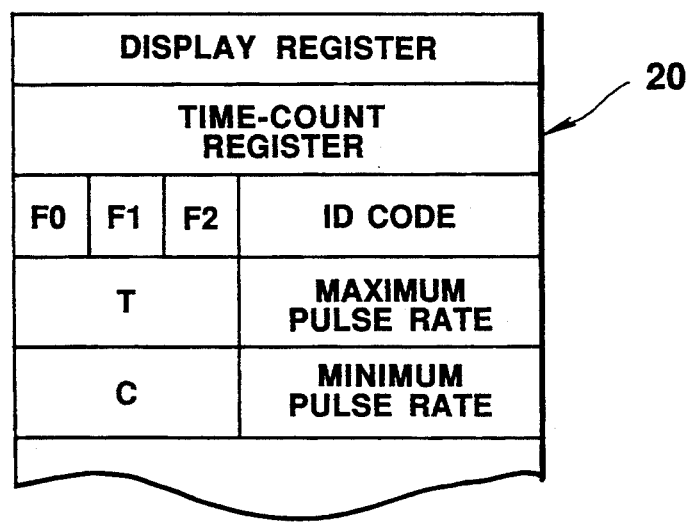
FIG. 13 is a view showing the memory format of a RAM shown in FIG. 11.

FIG. 13 is a view showing the memory format of the RAM 20 shown in FIG. 11.

Referring to FIG. 13, a display register stores data to be displayed on a display 24, and a time-count register stores current time data to be sequentially updated by time-count processing. A flag register F0 stores a flag indicating a condition of detection of a pulse rate signal, a flag register F1 stores a flag indicating a condition of setting of ID code data, and a flag register F2 stores a flag indicating a condition of alarming. An ID code register stores ID code data. The ID code data is, e.g., code data of eight bits set for each person to be monitored. Assume, for example, that ID code data for a person A to be monitored is "00000001" and ID code data for a person B to be monitored is "00000010". A register T is for measuring a period T of an electrocardiogram waveform signal as shown in FIG. 9C of the above first embodiment. A register C is for measuring an alarm time. A maximum pulse rate register stores maximum pulse rate data indicating the upper limit of pulse rate data. A minimum pulse rate register stores minimum pulse rate data indicating the lower limit of pulse rate data.

Figure 14:
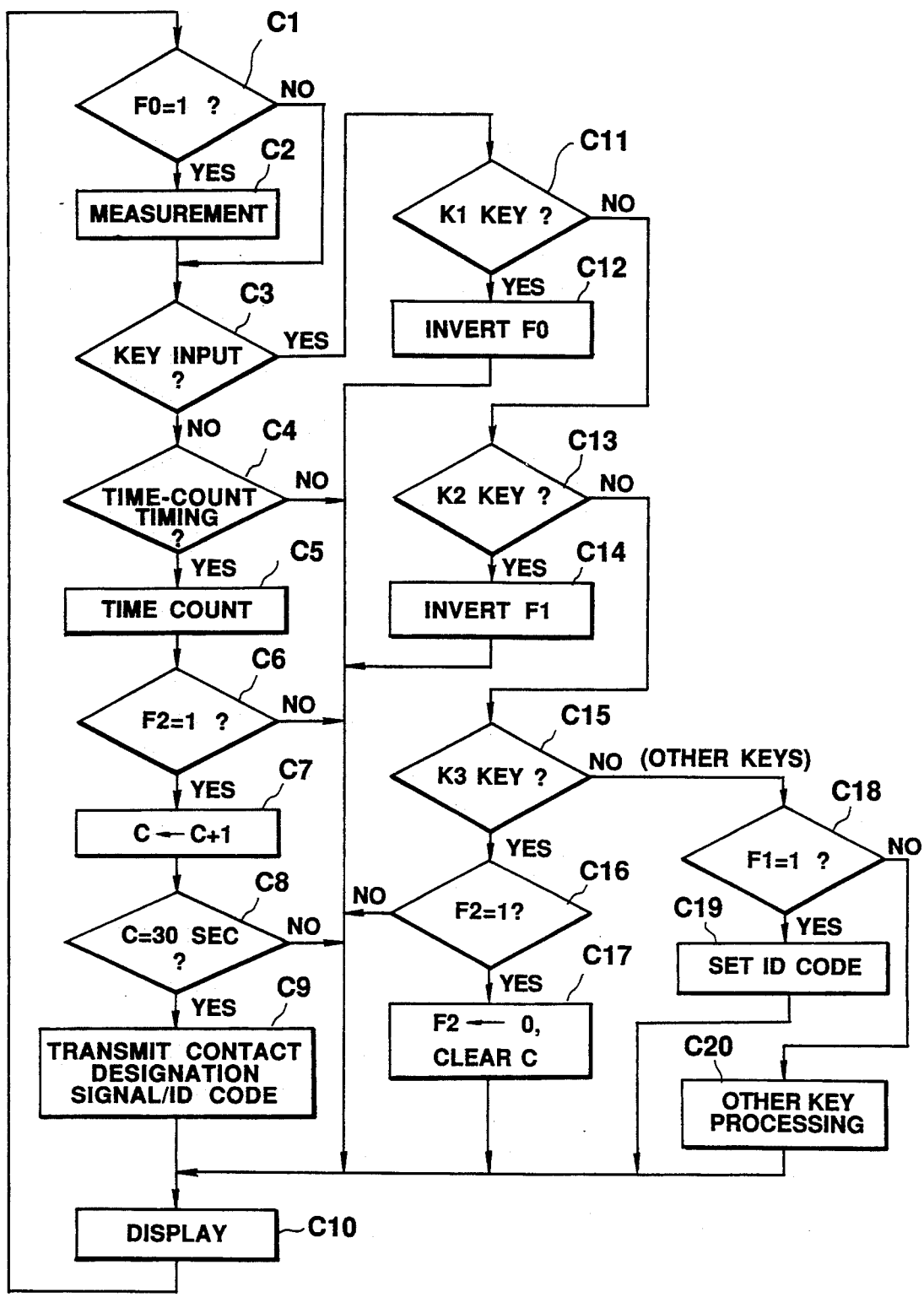
FIG. 14 is a flow chart for explaining the operation of a controller shown in FIG. 11.
Figure 15:
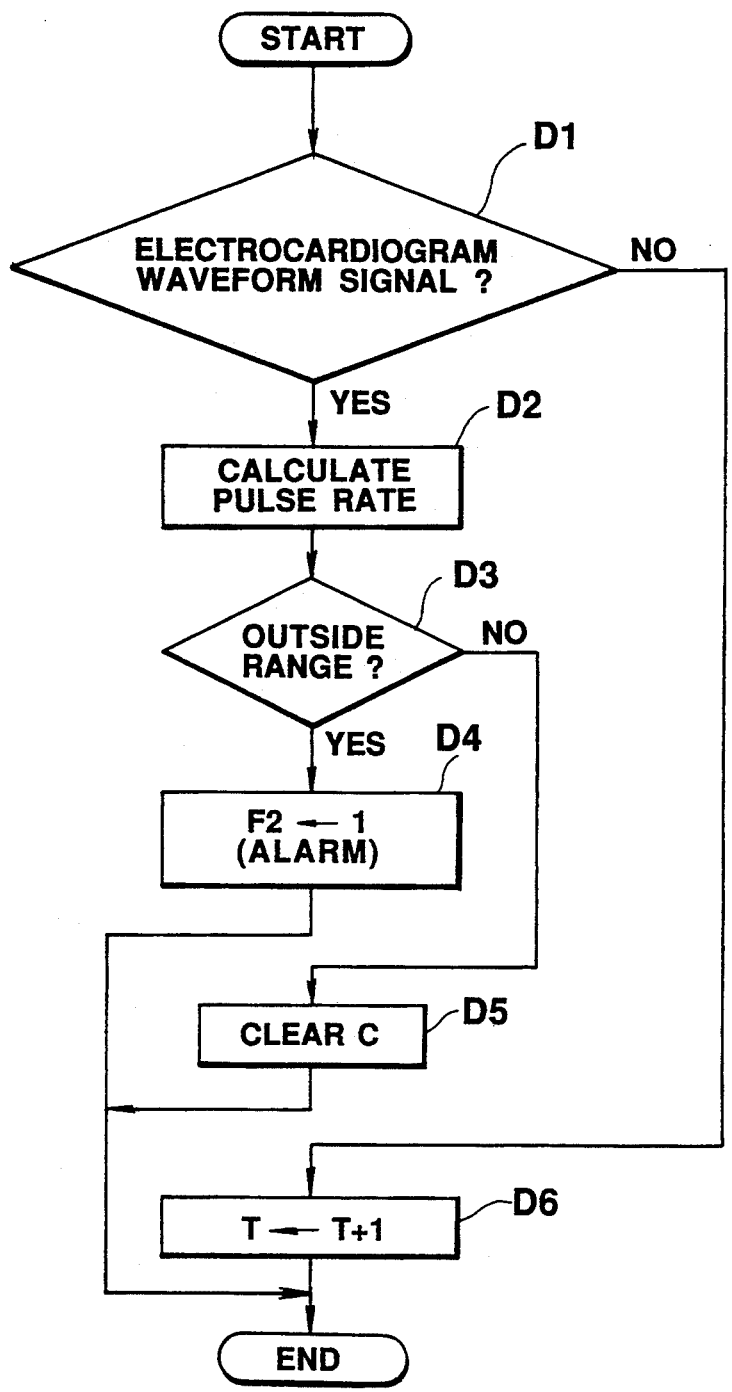
FIG. 15 is a flow chart for explaining the operation of the controller shown in FIG. 11.

The operations of this embodiment of the present invention will now be described below with reference to FIGS. 14 and 15. FIG. 14 is a flow chart showing the overall operation of the wristwatch 3 according to this embodiment.

Referring to FIG. 14, a controller 18 checks in step C1 whether "F0=1", i.e., the content of the flag register F0 is "1". If YES is determined in step C1, the flow advances to step C2. If NO is determined in step C1, the flow advances to step C3. If the K1 key 25a for pulse rate measurement is manipulated to set pulse rate measurement, "F0=1" is determined. Otherwise, "F0=0" is determined.

If F0=1" in step C1, the flow advances to step C2. In step C2, pulse rate measurement processing is executed. The details of this pulse rate measurement processing will be described later with reference to FIG. 15.

In subsequent step C3, the controller 18 checks whether a key input is present, i.e., any of the K1 to K3 keys 25a to 25c and other keys is manipulated on the key input unit 25. If YES in step C3, the flow advances to step C7. If NO in step C3, the flow advances to step C4.

If no key is manipulated yet, NO is determined in step C3, and the flow advances to step C4. In step C4, the controller 18 checks whether a time-count timing is set, i.e., a time-count signal is generated. If YES is determined in step C4, the flow advances to step C5. If NO is determined in step C4, the flow advances to step C6.

If the time-count timing is set in step C4, the flow advances to step C5 to execute time-count processing. That is, the current time data stored in the time-count register of the RAM 20 is updated.

In subsequent step C6, the controller 18 checks whether "F2=1". If YES in step C6, the flow advances to step C7. If NO in step C6, the flow advances to step C10. The flag register F2 is a register for storing a condition of execution of alarm processing, and "F2=1" means that alarming is currently being executed.

If no alarming is currently being executed so "F2=0", the flow advances from step C6 to step C10. In display processing in step C10, the data stored in the display register is displayed on the display 24. Thereafter, the flow returns to step C1.

If "F2=1", i.e., alarming is currently being executed, the flow advances from step C6 to step C7. In step C7, the content of the register C is incremented by one to measure the alarm time. In step C8, the controller 18 checks whether "C=30 seconds", i.e., the content of the register C has reached a value corresponding to "30 seconds". If the alarm time has not reached 30 seconds, NO is determined in step C8, and the flow advances to step C10. If the alarm time has reached 30 seconds, YES is determined in step C8, and the flow advances to step C9.

In step C9, a transmitter 22 transmits a contact designation signal indicating an abnormality in pulse rate data and ID code data stored in the RAM 20. That is, the controller 18 outputs the contact designation signal and the ID code data to a serial converter 21. The serial converter 21 converts the input contact designation signal and ID code data from the controller 18 into a serial signal and applies it to the transmitter 22. The transmitter 22 converts the input serial signal into a radio signal and transmits it from the antenna 5. The receiver unit 6 receives the contact designation signal and the ID code data in the form of a radio signal through the antenna 7 and sends it to the auto-dialing unit 80. In this case, the receiver unit 6 distinguishes a given contact designation signal from another on the basis of their ID code data. Therefore, even if contact designation signals are transmitted from a plurality of the wristwatches 3, a contact designation signal for a given person to be monitored can be discriminated from another. The auto-dialing unit 80 performs automatic dialing in accordance with a telephone number corresponding to the received ID code data. After executing the processing in step C9, the flow advances to step C10.

If any of the K1 to K3 keys 25a to 25c and other keys is manipulated on the key input unit 25, the flow advances from step C3 to step C11. In step C11, the controller 18 checks whether the K1 key 25a for pulse rate measurement is manipulated. If YES is determined in step C11, the flow advances to step C12. If NO is determined in step C11, the flow advances to step C13.

If manipulation of the K1 key 25a is determined in step C11, the flow advances to step C12, and the content of the flag register F0 is inverted like "0→1" or "1→0". After executing the processing in step C12, the flow advances to the display processing in step C10. If a key other than the K1 key 25a for pulse rate measurement is manipulated in step C11, the flow advances to step C13.

In step C13, the controller 18 checks whether the K2 key 25b for setting ID code data is manipulated. If YES in step C13, the flow advances to C14. If NO in step C13, the flow advances to step C15. If manipulation of the K2 key 25b is determined in step C13, the flow advances to step C14, and the content of the flag register F1 is inverted like "0→1" or "1→0". After executing the processing in step C14, the flow advances to step C10.

If a key other than the K1 key 25a for pulse rate measurement and the K2 key 25b for setting ID code data is manipulated, NO is determined in each of steps C11 and C13, and the flow advances to step C15. In step C15, the controller 18 checks whether the K3 key 25c for stopping an alarm sound is manipulated. If YES in step C15, the flow advances to step C16. If NO in step C15, the flow advances to step C10.

If manipulation of the K3 key 25c is determined in step C15, the flow advances from step C15 to step C16, and the controller 18 checks whether "F2=1". If YES is determined in step C16, the flow advances to step C17. If NO is determined in step C16, the flow advances to step C10. As described above, the flag register F2 stores a condition of execution of alarm processing, and "F2=1" means that alarming is currently being executed.

If "F2=1" is determined, the flow advances from step C16 to step C17. In step C17, "0" is written in the flag register F2, and the content of the register C is cleared to reset the alarm time to "0". The flow advances from step C17 to step C10.

If numeric keys, for example, are manipulated as other keys to input numerical data in step C15, the flow advances to step C18. In step C18, the controller 18 checks whether "F1=1". If YES in step C18, the flow advances to step C19. If NO in step C18, the flow advances to step C20.

If "F1=1" is determined in step C18, this means that setting of ID code data is required, so the flow advances to step C19 to store the input numerical data as ID code data in the ID code data register of the RAM 20. After executing the processing in step C19, the flow advances to step C10.

If "F1=1" is not determined in step C18, the flow advances to step C20 to execute other processing (e.g., time setting, or setting of maximum or minimum pulse rate data), and the flow advances to step C10.

The details of the pulse rate measurement processing will be described below with reference to FIG. 15.

In step D1, the controller 18 checks whether an electrocardiogram waveform signal is present.

That is, the controller 18 checks whether an electrocardiogram waveform signal transmitted by electromagnetic induction from the shirt 1 is detected by the receiving coil 4. If YES is determined in step D1, the flow advances to step D2. If NO is determined in step D1, the flow advances to step D6.

If no electrocardiogram waveform signal is detected yet in step D1, the flow advances to step D6. In step D6, the content of the register T is incremented by one.

That is, the register T measures a period T from a preceding electrocardiogram waveform signal to a current electrocardiogram waveform signal. After executing the processing in step D6, the pulse rate measurement processing shown in FIG. 8 is ended.

If an electrocardiogram waveform signal is detected, YES is determined in step D1, and processing in step D2 is executed. In step D2, pulse rate calculation processing is executed. That is, since the period T from a preceding electrocardiogram waveform signal to a current electrocardiogram waveform signal is measured by the register T, pulse rate data is calculated on the basis of this measured time.

In subsequent step D3, the controller 18 checks whether the calculated pulse rate data falls outside the range of the maximum and minimum pulse rate data prestored in the RAM 20.

If the pulse rate data falls outside this range, YES is determined in step D3, and the flow advances to step D4. In step D4, "1" is written in the flag register F2 to set alarm processing, and the controller 18 outputs an alarm signal to an alarm unit 26, thereby causing the alarm unit 26 to generate an alarm sound. If a patient as a person to be monitored who notices this alarm sound actually feels that the physical condition becomes worse, he or she leaves the alarm sound generated. If, on the other hand, the patient determines that the detection of an abnormality in pulse rate data is an erroneous operation, he or she stops the alarm sound by manipulating the K3 key 25c for stopping an alarm sound.

If the alarm sound is not stopped by manipulation of the K3 key 25c performed by the person to be monitored and 30 seconds have elapsed since the alarm sound began, YES is determined in step C8 of FIG. 14, and the processing in step C9 is executed. That is, the wristwatch 3 transmits a contact designation signal and ID code data. The receiver unit 6 receives these signals, and the auto-dialing unit 80 immediately performs automatic dialing.

If the alarm sound is generated by an erroneous operation of the wristwatch 3, the person to be monitored manipulates the K3 key 25c for stopping an alarm sound at once. Therefore, the processing in step C17 is executed to disable the alarm processing, thereby immediately stopping the alarm sound currently being generated. After executing the processing in step D4, the pulse rate measurement processing shown in FIG. 15 is ended.

If the value of pulse rate data falls within the predetermined range, NO is determined in step D3, and the flow advances to step D5. In step D5, the content of the register T is cleared, and the pulse rate measurement processing of FIG. 15 is ended.

In hospitals and the like, a system in which each patient pushes a button provided at a bedside when his or her condition gets worse and in this manner informs nurses of the state of emergency is generally put into practical use. In this system, however, if the condition of a patient is so bad that he or she cannot push the button himself or herself, it is impossible to inform nurses of this emergent state. For this reason, an automatic emergency informing system has been planned in which the conditions of patients are monitored constantly, and if an abnormality is detected in a given patient, an emergency contact center, such as a nurse center, is automatically informed of this detection of the abnormality.

In such an automatic emergency informing system, however, even if a detector erroneously detects an abnormality in a patient, this erroneous detection is automatically transmitted without the will of the patient. Therefore, the load on nurses or the like may be increased due to false emergency contacts caused by these erroneous operations.

This embodiment adopts the arrangement as described above in order to eliminate this conventional inconvenience. Therefore, it is possible to prevent a false emergency contact caused by an erroneous operation.

Note that in each of the above embodiments, pulse rate data is monitored constantly. However, the data may be monitored for each predetermined time interval such as 30 seconds or one minute. In addition, biological data to be monitored is not limited to pulse rate data but may be electrocardiogram waveform data corresponding to an electrocardiogram waveform signal, blood pressure data, or body temperature data.

Furthermore, in the above embodiments, the monitor unit generates an alarm sound when the value of pulse rate data of a person to be monitored falls outside a predetermined range. However, this alarm sound may also be generated by the alarm unit 26 of the wristwatch 3. In addition, the portable electronic instrument is not limited to a wristwatch to be put on a wrist but may be an electronic instrument to be put on an arm or an electronic instrument having a size capable of being put into a pocket.

A personal computer or the like may also be used as the monitor unit.

Still another embodiment of the present invention will be described below with reference to FIGS. 16 to 22.

Figure 16:
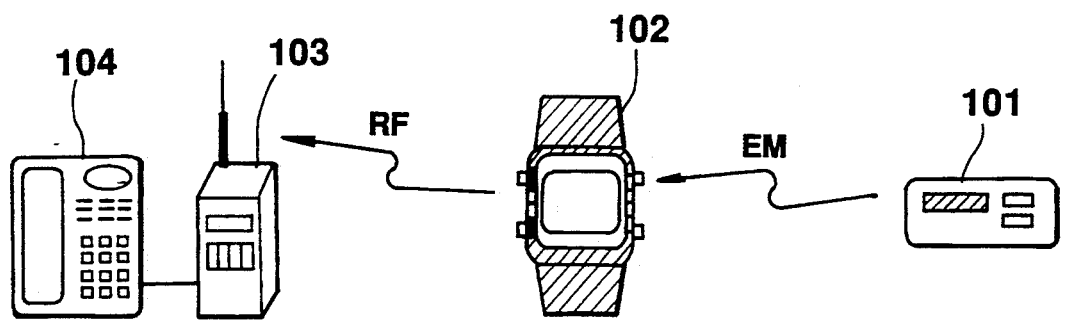
FIG. 16 is a view showing a monitor system according to still another embodiment of the present invention.

FIG. 16 is a view showing a monitor system according to this embodiment.

Referring to FIG. 16, reference numeral 101 denotes a detector unit to be put directly on a portion of a body of a person to be monitored where a heartbeat can be reliably detected, such as a lower portion of the left chest. The detector unit 101 transmits a detected heartbeat signal by electromagnetic induction (represented by "EM" in FIG. 16). Reference numeral 102 denotes a receiver to be put on, e.g., the left wrist of a person to be monitored. The receiver 102 receives the heartbeat signal transmitted by electromagnetic induction from the detector unit 101 and displays the heart rate. The receiver 102 also stabilizes the heartbeat signal by performing error correction for the signal and then performs abnormality check of the heartbeat. If an abnormality is detected, the receiver 102 superposes a signal indicating occurrence of the abnormality on a carrier frequency (represented by RF in FIG. 16) and transmits the signal as a radio signal. Reference numeral 103 denotes a managing unit connected to, e.g., a telephone set 104. The managing unit 103 receives the signal indicating occurrence of the abnormality superposed on the carrier frequency and transmitted from one or a plurality of receivers 102 and informs doctors or nurses of this reception of the signal. The detector unit 101, the receiver 102, and the managing unit 103 constitute a constant heartbeat monitor system according to this embodiment of the present invention.

Figure 17:
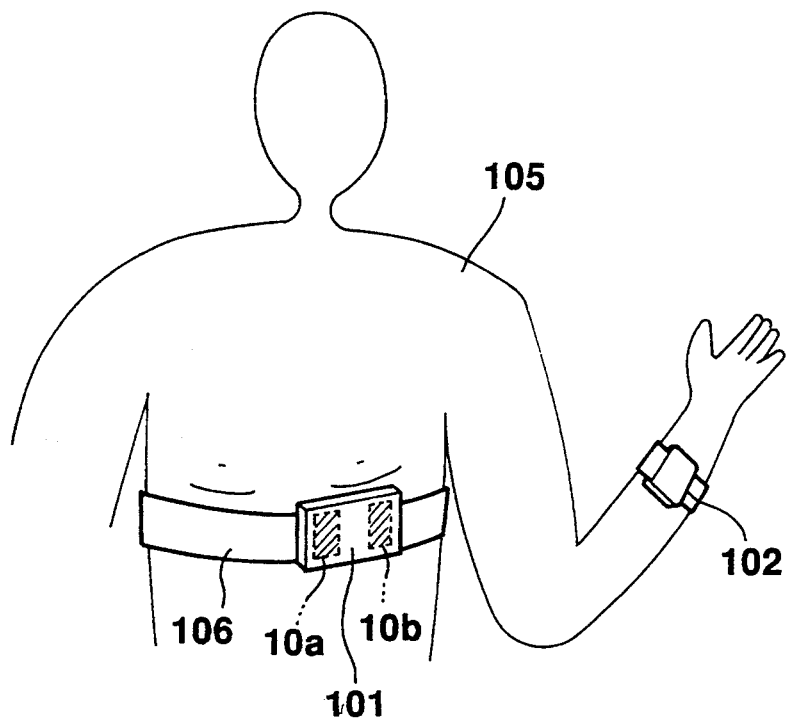
FIG. 17 is a view showing a condition in that a detector unit and a receiver shown in FIG. 16 are put on a person to be monitored.

FIG. 17 is a view showing a condition in which the detector unit 101 and the receiver 102 are put on a person 105 to be monitored. As shown in FIG. 17, the detector unit 101 is fixed by a band 106 or the like on a lower portion of the left chest of the person 105 where a heartbeat can be reliably detected, such that a pair of electrodes 10a and 10b projecting from its surface are brought into contact with the skin of a body portion immediately above the heart. A heartbeat detected by the detector unit 101 is signalized into a predetermined pattern and transmitted by electromagnetic induction within an effective range of, e.g., 70 to 80 cm. This electromagnetic induction signal is received by the wristwatch-like receiver 102 put on the left wrist of the person 105.

The receiver 102 performs error correction, i.e., noise removal and interpolation for the received heartbeat signal of electromagnetic induction in accordance with the above pattern. Thereafter, the receiver 102 restores the original heartbeat signal using a complementary pattern of the above pattern, calculates a heart rate, and checks the presence/absence of an abnormality such as arrhythmia. If an abnormality is detected, the receiver 102 transmits a radio signal indicating occurrence of the abnormality to the managing unit 103 not shown in FIG. 17.

Figure 18:
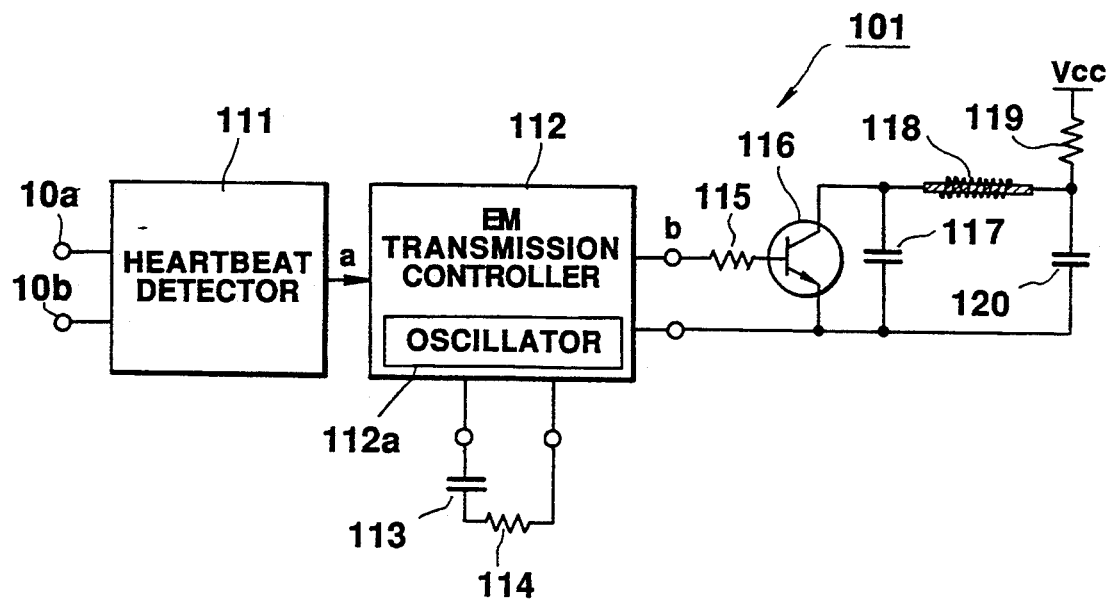
FIG. 18 is a block diagram showing the circuit configuration of the detector unit shown in FIG. 16.

FIG. 18 shows the arrangement of an electronic circuit provided in the detector unit 101. Referring to FIG. 18, reference numeral 111 denotes a heartbeat detector for amplifying the myoelectric potential difference of a human body obtained by the pair of electrodes 10a and 10b in contact with the above predetermined portion of the person 105 to be monitored. The detector 111 then filters the amplified potential difference to generate a heartbeat signal a and outputs the signal to an EM transmission controller 112.

The EM transmission controller 112 has an internal oscillator 112a. In addition, a capacitor 113 and a resistor 114 are externally connected in series with the controller 112. The EM transmission controller 112 converts the heartbeat signal a from the heartbeat detector 111 into a patterned heartbeat signal b and outputs the signal to the base electrode of an NPN transistor 116 via a resistor 115.

A capacitor 117 is connected between the collector and emitter electrodes of the transistor 116. The collector electrode is connected to one terminal of an electromagnetic induction coil 118, and the emitter electrode is connected to the EM transmission controller 112. A voltage VCC is applied to the other terminal of the electromagnetic induction coil 118 and one terminal of a capacitor 120 through a resistor 119. The other terminal of the capacitor 120 is connected to the emitter electrode of the transistor 116.

Figure 19:
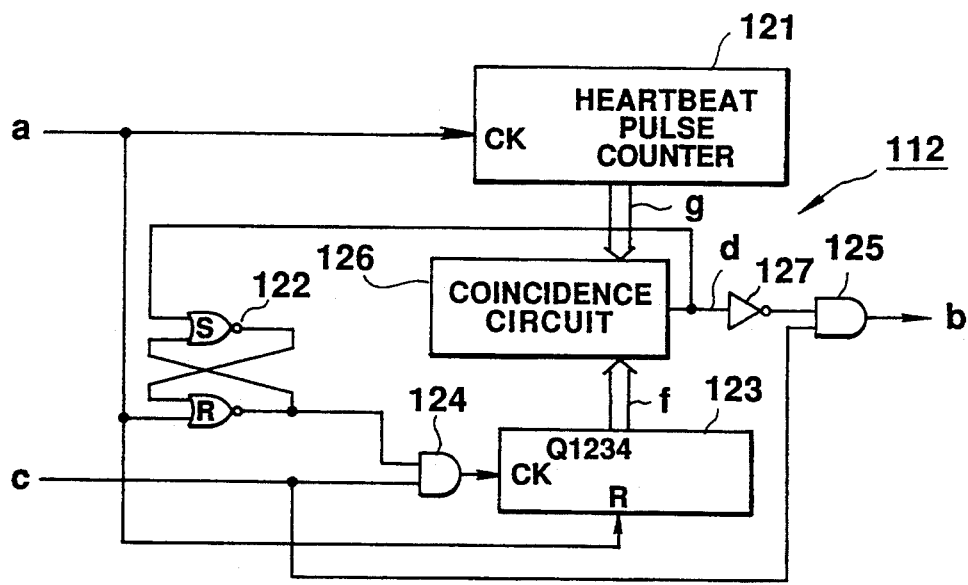
FIG. 19 is a block diagram showing the circuit configuration of a transmission controller incorporated in the detector unit shown in FIG. 18.

FIG. 19 shows the circuit configuration of the EM transmission controller 112. Referring to FIG. 19, the input heartbeat signal a from the heartbeat detector 111 is applied to a clock terminal CK of a heartbeat pulse counter 121, the reset terminal of a flip-flop (to be referred to as an F/F hereinafter) 122 constituted by two NOR gates, and a reset terminal R of a clock counter 123. A fundamental clock c is applied to AND gates 124 and 125 from the internal oscillator 112a.

The heartbeat pulse counter 121 is a base-n counter for sequentially counting pulses of the heartbeat signal a. In this embodiment, the counter 121 operates as a ternary counter (n=3), and its count g is supplied to a coincidence circuit 126. A coincidence signal d from the coincidence circuit 126 is applied to the set terminal of the F/F 122, and an inverted output of the signal is applied to the AND gate 124 as a gate control signal. The AND gate 124 operates as a clock gate and applies its output to a clock terminal CK of the clock counter 123.

The clock counter 123 is a four-bit counter for counting pulses of the fundamental clock c applied via the AND gate 124 after being reset by the heartbeat signal a. Two upper bits of the clock counter 123 are supplied as a count f to the coincidence circuit 126.

The coincidence circuit 126 compares the count g from the heartbeat pulse counter 121 with the count f from the clock counter 123. If a coincidence is determined, the coincidence circuit 126 inverts the coincidence signal d through the set terminal of the F/F 122 and an inverter 127 and sends the inverted signal to the AND gate 125. The output from the AND gate 125 is supplied as a heartbeat signal b to the base electrode of the transistor 116 via the resistor 115.

Figure 20:
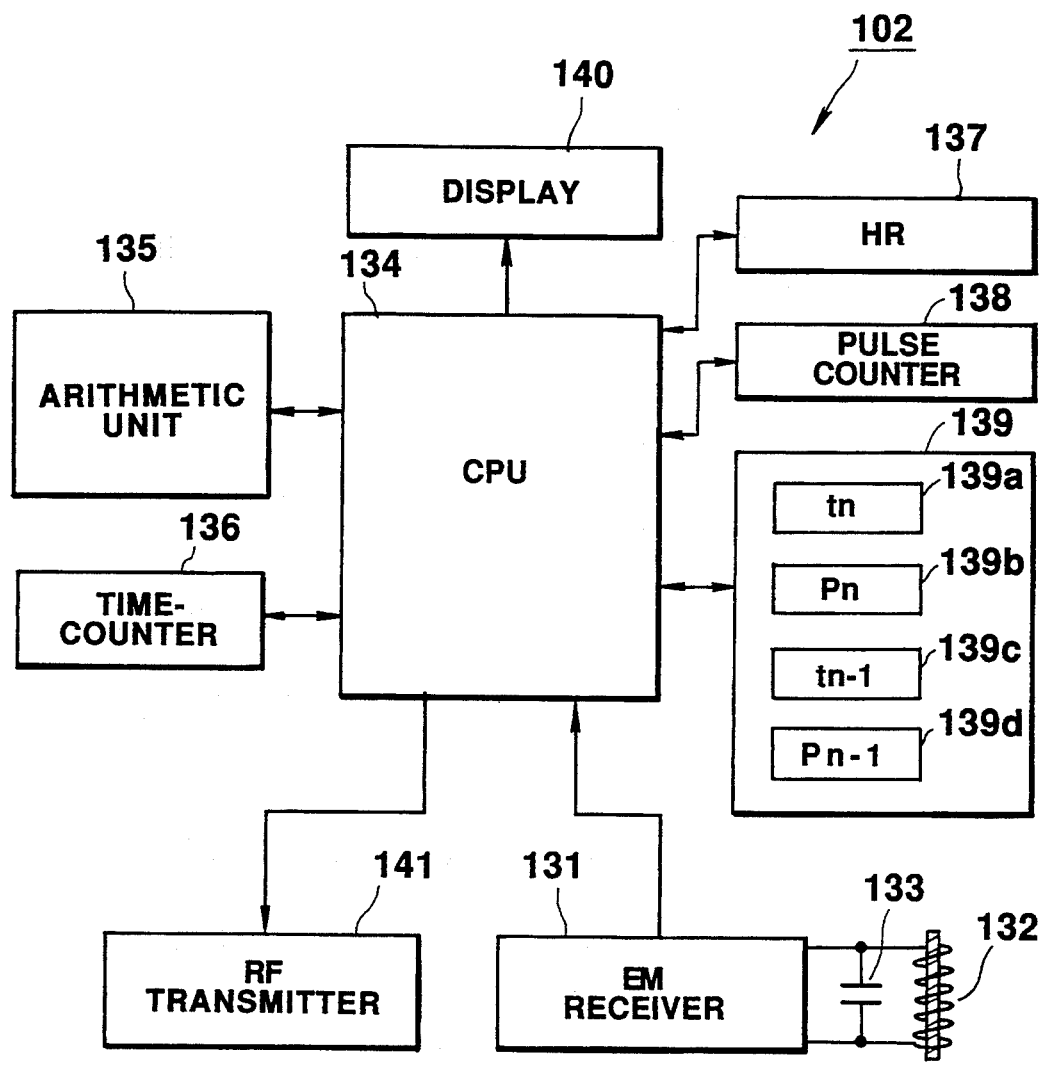
FIG. 20 is a block diagram showing the circuit configuration of a receiver shown in FIG. 16.

FIG. 20 shows the internal circuit configuration of the receiver 102. Referring to FIG. 20, electromagnetic induction obtained by the electromagnetic induction coil 118 of the detector unit 101 is frequency-selected and received by an electromagnetic induction coil 132. The coil 132 and a capacitor 133 are connected in parallel with an EM receiver 131. The EM receiver 131 converts the received electromagnetic induction into a pulse signal and sends the signal to a CPU 134.

The CPU 134 controls operations of the individual circuits in the receiver 102 on the basis of the signal from the EM receiver 131. The CPU 134 is connected to an arithmetic unit 135 for calculating a heart rate and the like, a time-counter 136 for performing a time-count operation, and a heart rate register (represented by "HR" in FIG. 20) 137 for holding a heart rate. The CPU 134 is also connected to a pulse counter 138 for counting pulse signals from the EM receiver 131, and a register unit 139 including a tn register 139a, a pn register 139b, a tn-1 register 139c, and a pn-1 register 139d. The register unit 139 reversely patterns the signal from the EM receiver 131. The CPU 134 outputs data to be displayed, such as a time and a heart rate, to a display 140 constituted by liquid crystal display elements, and a signal indicating occurrence of an abnormality to an RF transmitter 141.

The RF transmitter 141 superposes the signal indicating occurrence of an abnormality supplied from the CPU 134 on a carrier frequency and transmits the signal to the managing unit 103 shown in FIG. 16.

The operation of the above embodiment will be described below.

An operation of generating the patterned heartbeat signal b from the heartbeat signal a performed by the EM transmission controller 112 of the detector unit 101 will be described first with reference to FIG. 21.

Figure 21:
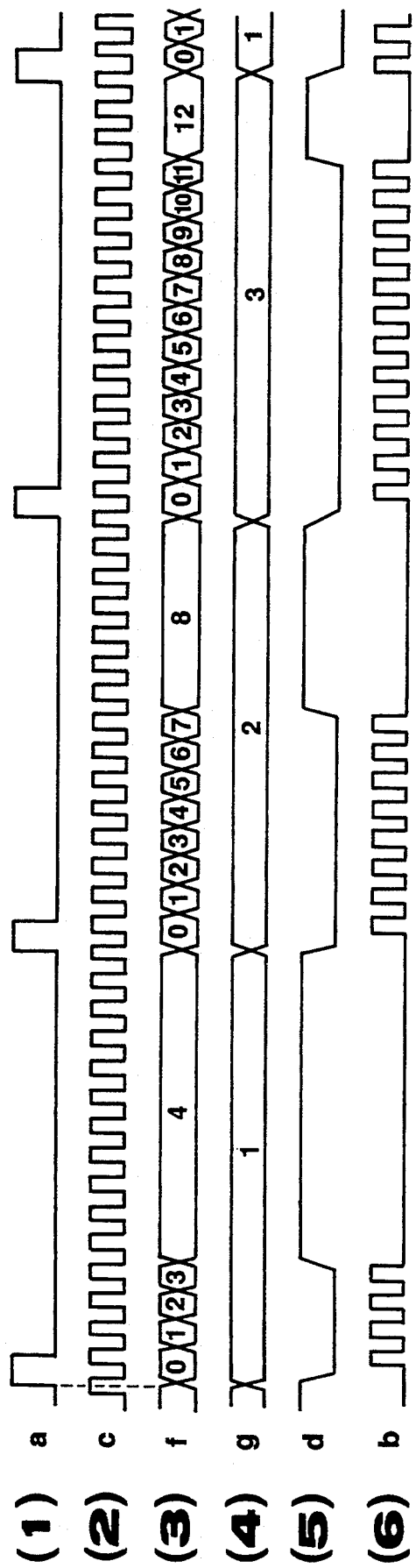
FIG. 21 is a timing chart showing conditions of signal processing performed by a transmission controller incorporated in the detector unit shown in FIG. 18.

As indicated by (1) in FIG. 21, pulses of the heartbeat signal a supplied from the heartbeat detector 111 are counted by the heartbeat pulse counter 121 as a ternary counter in the EM transmission controller 112. The count is set at "1" as an initial value as indicated by (4) in FIG. 21, and the F/F 122 and the clock counter 123 are reset.

Resetting of the F/F 122 enables the AND gate 124, so pulses of the fundamental clock c indicated by (2) in FIG. 21 are counted by the clock counter 123 via the AND gate 124 as indicated by (3) in FIG. 21.

As described above, this clock counter 123 is a four-bit counter, and its two upper bits are supplied as the count f to the coincidence circuit 126. While the count of the clock counter 123 is "0 (0000)" to "3 (0011)", the value of its two upper bits is "00". Therefore, the coincidence circuit 126 determines that the count "1" of the heartbeat pulse counter 121 does not coincide with the count of the clock counter 123 and sets its coincidence signal d to level "L" as indicated by (5) in FIG. 21. This coincidence signal d is inverted to level "H" by the inverter 127, and this enables the AND gate 125. Therefore, as indicated by (6) in FIG. 21, four pulses of the fundamental clock c are directly output as the heartbeat signal b via the AND gate 125.

Thereafter, when the input fundamental clock c to the clock counter 123 increments its count to "4 (0100)", the value of the two upper bits of the counter 123 becomes "01". The coincidence circuit 126 determines that this value coincides with the count "1" of the heartbeat pulse counter 121 and raises its coincidence signal d from level "L" to "H" as indicated by (5) in FIG. 21. This coincidence signal d sets the F/F 122 to disable the AND gate 124, thereby stopping the count operation of the clock counter 123. The coincidence signal is also inverted to level "L" by the inverter 127, and this disables the AND gate 125. As a result, after four pulses of the fundamental clock c are successively output, the heartbeat signal b is kept at level "L" until the next pulse of the heartbeat signal a is applied.

The next input pulse of the heartbeat signal a increments the count of the heartbeat pulse counter 121 to "2 (10)" and resets the F/F 122 and the clock counter 123 again.

Similarly, while the count of the clock counter 123 is "0 (0000)" to "7 (0111)", the coincidence circuit 126 determines that the count "2 (10)" of the heartbeat pulse counter 121 does not coincide with the count of the clock counter 123 and sets its coincidence signal d to level "L" as indicated by (5) in FIG. 21. This coincidence signal d is inverted to level "H" by the inverter 127, and this enables the AND gate 125. Therefore, as indicated by (6) in FIG. 21, eight pulses of the fundamental clock c are directly output as the heartbeat signal b via the AND gate 125.

Thereafter, when the input fundamental clock c to the clock counter 123 increments its count to "8 (1000)", the value of the two upper bits of the clock counter 123 becomes "10". Therefore, the coincidence circuit 126 determines that this value coincides with the counter "2 (10)" of the heartbeat pulse counter 121 and raises its coincidence signal d from level "L" to "H" as indicated by (5) in FIG. 21. This coincidence signal d sets the F/F 122 to disable the AND gate 124, thereby stopping the count operation of the clock counter 123. The coincidence signal d is also inverted to level "L" by the inverter 127, and this disables the AND gate 125. As a result, after eight pulses of the fundamental clock c are successively output, the heartbeat signal b is kept at level "L" until the next pulse of the heartbeat signal a is input.

The next input pulse of the heartbeat signal a increments the count of the heartbeat pulse counter 121 to "3 (11)" and resets the F/F 122 and the clock counter 123 again.

As described above, while the count of the clock counter 123 is "0 (0000)" to "11 (1011)", the coincidence circuit 126 determines that the count "3 (11)" of the heartbeat pulse counter 121 does not coincide with the count of the clock counter 123 and sets its coincidence signal d to level "L" as indicated by (5) in FIG. 21. This coincidence signal d is inverted to level "H" by the inverter 127, and this enables the AND gate 125. Therefore, as indicated by (6) in FIG. 21, twelve pulses of the fundamental clock c are directly output as the heartbeat signal b via the AND gate 125.

Thereafter, when the input fundamental clock c to the clock counter 123 increments its count to "12 (1100)", the value of the two upper bits of the clock counter 123 becomes "11". Therefore, the coincidence circuit 126 determines that this value coincides with the count "3 (11)" of the heartbeat pulse counter 121 and raises its coincidence signal d from level "L" to "H" as indicated by (5) in FIG. 21. This coincidence signal d sets the F/F 122 to disable the AND gate 124, thereby stopping the count operation of the clock counter 123. The coincidence signal d is also inverted to level "L" by the inverter 127, and this disables the AND gate 125. As a result, after twelve pulses of the fundamental clock c are successively output, the heartbeat signal b is kept at level "L" until the next pulse of the heartbeat signal a is input.

In this manner, each time the pulse of the heartbeat signal a is applied, the EM transmission controller 112 outputs the fundamental clock c as the heartbeat signal b in accordance with a predetermined pattern of the number of pulses of "four", "eight", "twelve", "four", "eight", "twelve". . . .

This heartbeat signal b controls switching of the transistor 116, and the electromagnetic induction coil 118 is excited by the voltage $V_{CC}$ to generate an electromagnetic induction signal.

Figure 22:
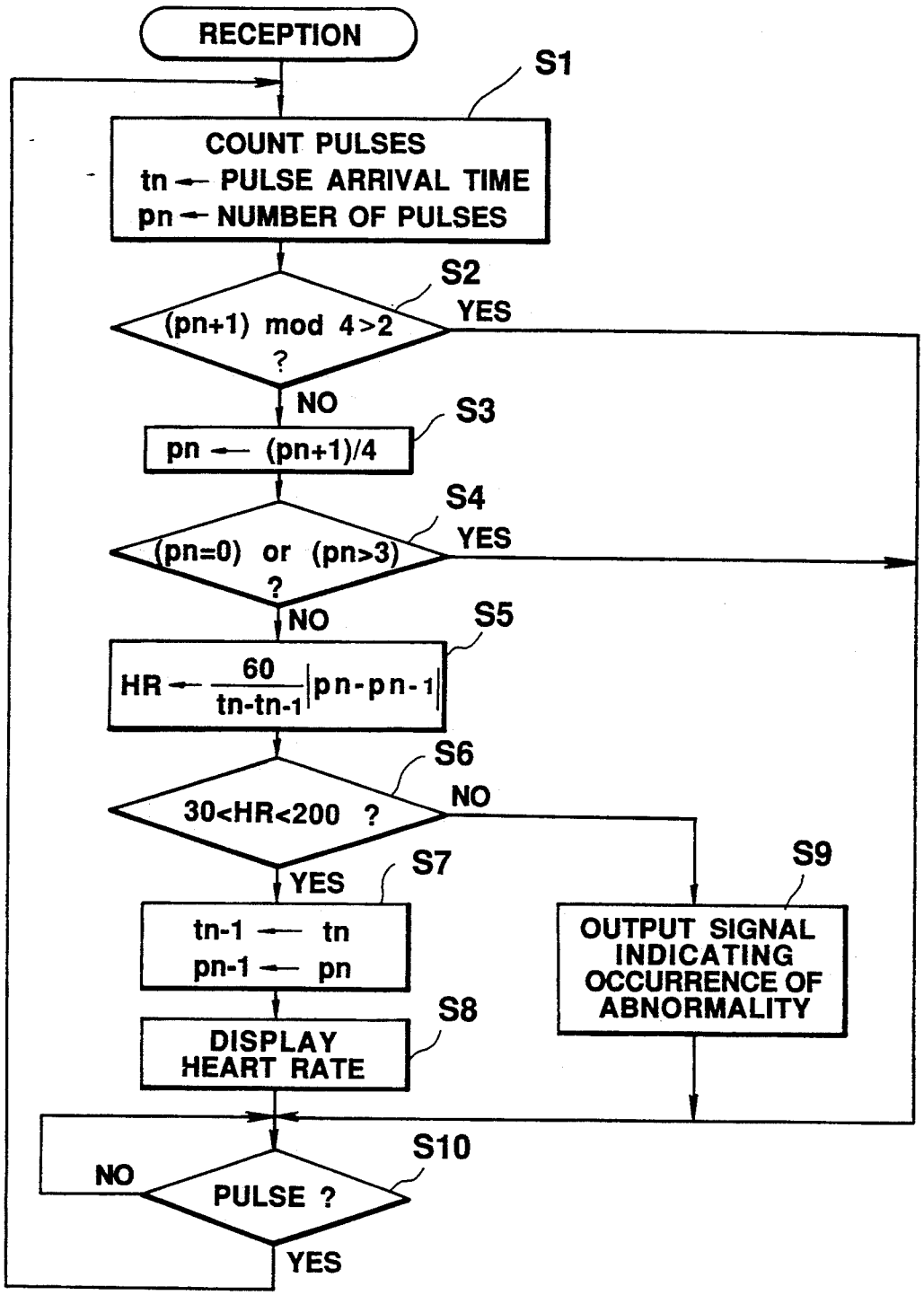
FIG. 22 is a flow chart for explaining the operation of a controller shown in FIG. 16.

In the receiver 102, on the other hand, the CPU 134 performs reception processing as shown in FIG. 22 for the electromagnetic induction signal transmitted from the detector unit 101 as described above, in accordance with programs stored in an internal ROM (not shown).

The processing shown in FIG. 22 is executed when the EM receiver 131 pulses a signal received by the electromagnetic induction coil 132 and sends the pulsed signal to the CPU 134. In step S1, the CPU 134 causes the pulse counter 138 to count the input successive pulses from the EM receiver 131 and holds the number of pulses in the pn register 139b of the register unit 139. At the same time, the CPU 134 reads out time data from the time-counter 136 at the time the pulse count is started and holds the readout data in the tn register 139a of the register unit 139.

In step S2, the CPU 134 increments the number of pulses held in the pn register 139b by one to obtain a value "pn+1" and checks by using the arithmetic unit 135 whether a value as a remainder obtained by dividing the value "pn+1" by a constant "4" is larger than a constant "2". This is performed in order to check whether "three to five", "seven to nine", or "eleven to thirteen" successive pulses are received while an error of "q1" is allowed for signals transmitted in accordance with the predetermined pattern of "four", "eight", or "twelve" pulses. If the remainder is larger than "2", i.e., the remainder is "3", the CPU 134 determines that the received signal is electromagnetic noise. In subsequent step S10, therefore, the CPU 134 waits for the next pulse reception. If a pulse is received, the CPU 134 repeats the processing from step S1.

If the CPU 134 determines in step S2 that the remainder obtained by dividing "pn+1" by the constant "4" is "2" or less, the flow advances to step S3. In step S3, the CPU holds the integral part of the quotient obtained by dividing "pn+1" by the constant "4" in the pn register 139b of the register 139.

This value held in the pn register 139b is supposed to coincide with one of the counts "1", "2", and "3" of the heartbeat pulse counter 121 of the EM transmission controller 112 of the detector unit 101. Therefore, in subsequent step S4, the CPU 134 checks whether the value held in the pn register 139b is equal to "0" or larger than a constant "3".

If the value held in the pn register 139b is equal to "0" or larger than the constant "3", the value does not coincide with possible values of the heartbeat pulse counter 121. Therefore, the CPU 134 determines that this received pulse is also electromagnetic noise, and waits for the next pulse reception in step S10. If a pulse is received, the CPU 134 repeats the processing from step S1.

If the CPU 134 determines in step S4 that the value held in the pn register 139b is one of "1", "2", and "3", it recognizes that the received pulse is a correct one transmitted from the detector unit 101. Therefore, the CPU 134 causes the arithmetic unit 135 to perform the following operation using the values held in the tn register 139a, the pn register 139b, the tn−1 register 139c, and the pn−1 register 139d of the register unit 139:

$$(60/(tn-tn-1))\cdot|pn-pn-1| \quad (1)$$

The CPU 134 holds the operation result as a heart rate in the heart rate register 137. In a part "60/(tn−tn−1)" of equation (1), a constant "60" is divided by a time difference between time data "tn" corresponding to a current pulse reception timing and time data "tn−1" corresponding to a preceding pulse reception timing, thereby obtaining the period of a heartbeat pulse. The result is multiplied by "|pn−pn−1|" to perform interpolation for a case wherein one of received pulses is omitted for some reason. The obtained calculation result is held as a heart rate per minute in the heart rate register 137.

Thereafter, the CPU 134 checks in step S6 whether this value held in the heart rate register 137 falls within a range of "30 to 200" which is generally considered to be normal.

If the value falls outside this range, the CPU 134 determines that the heartbeat of the person 105 to be monitored is abnormal. In step S9, the CPU 134 causes the RF transmitter 141 to transmit a signal indicating occurrence of the abnormality to the managing unit 103, thereby performing necessary alarm processing. Thereafter, in step S10, the CPU 134 waits for the next pulse reception. If a pulse is received, the CPU 134 repeats the processing from step S1.

If the value held in the heart rate register 137 falls within the range of "30 to 200" in step S6, the CPU 134 determines that the heartbeat is currently normal, and the flow advances to step S7. In step S7, the CPU 134 transfers the current data held in the tn register 139a and the pn register 139b to the tn−1 register 139c and the pn−1 register 139d, respectively, as preceding data, in order to prepare for the next pulse reception. In step S8, the CPU 134 causes the display 140 to display the heart rate held in the heart rate register 137. Thereafter, the CPU 134 waits for the next pulse reception in step S10.

Note that in the above embodiment, a ternary counter is used as the heartbeat pulse counter 121 of the EM transmission controller 112 to enable interpolation for pulses received by the receiver 102 even if one of the pulses is omitted for some reason, as indicated by "|pn−pn−1|" in equation (1). However, the use of a base-n counter (n>4) makes it possible to perform interpolation for omission of "n−2" pulses upon pulse reception.

According to this embodiment as described above, a heartbeat signal sensed by a sensor in the detector unit put directly on the body of a person to be monitored is regularly patterned in accordance with a predetermined pattern before transmission. The receiver for receiving this heartbeat signal transmitted from the detector unit performs error correction, such as noise removal and interpolation, for the heartbeat signal in accordance with the pattern and then executes necessary processing. This makes it possible to provide a constant heartbeat monitor system capable of correcting errors produced in an electromagnetic induction heartbeat signal which is easily affected by external electromagnetic noise during transmission and capable of performing calculation of a heartbeat or detection of an abnormality in a stable condition.

What is claimed is:

1. A monitor system comprising:
   first means which includes biological signal detecting means, which is put on a human body, for detecting a biological signal generated from the human body, and first signal transmitting means for transmitting said biological signal detected by said biological signal detecting means;
   second means which includes first signal receiving means for receiving said biological signal transmitted from said first signal transmitting means, said second signal transmitting means for transmitting, when an abnormality is detected in the value of said biological signal received by said first signal receiving means, said biological signal as a radio signal; and
   third means, which includes second signal receiving means for receiving said radio signal transmitted from said second signal transmitting means, for monitoring the abnormality on the basis of said radio signal,
   wherein said second means includes:
   detecting means for detecting the abnormality;
   alarm means for generating an alarm sound when the abnormality is detected by said detecting means;
   external operation switch means; and
   signal transmission controlling means for controlling said second signal transmitting means such that when said external switch means is operated during generating of the alarm sound, said second signal transmitting means is prohibited from transmitting said biological signal, and when said external operation switch means is not operated during generating of the alarm sound in a predetermined period of time, said second signal transmitting means transmits said biological signal as said radio signal.

2. The monitor system according to claim 1, wherein said second signal transmitting means of said second means includes means for transmitting an identification code signal for identifying said second means in addition to said biological signal.

3. The monitor system according to claim 1, further comprising memory means for storing an identification code signal for identifying said second means, and wherein said second signal transmitting means transmits said identification code signal in addition to said biological signal.

4. The monitor system according to claim 1, wherein said first signal transmitting means includes electromagnetic induction means for transmitting said biological signal from said first signal transmitting means.

5. The monitor system according to claim 1, wherein said second means is mountable on an arm of the human body.

6. The monitor system according to claim 1, wherein said biological signal generated from the human body is a signal indicating a pulse wave.

7. The monitor system according to claim 1, wherein when said external operation switch means is operated during generating of said alarm sound, said alarm means stops generating said alarm sound.

8. The monitor system according to claim 1, comprising a plurality of said first means and a plurality of said second means, and wherein said second signal receiving means of said third means receives radio signals transmitted from said plurality of second means.

* * * * *